(12) United States Patent  (10) Patent No.: US 7,699,861 B2
Bayer  (45) Date of Patent: Apr. 20, 2010

(54) CONDUIT HARVESTING INSTRUMENT AND METHOD

(75) Inventor: Hanspeter Robert Bayer, Meriden, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 1388 days.

(21) Appl. No.: 10/738,007

(22) Filed: Dec. 17, 2003

(65) Prior Publication Data

US 2004/0133228 A1 Jul. 8, 2004

Related U.S. Application Data

(63) Continuation of application No. PCT/US02/020450, filed on Jun. 26, 2002.

(60) Provisional application No. 60/301,059, filed on Jun. 26, 2001.

(51) Int. Cl.
*A61B 17/22* (2006.01)
(52) U.S. Cl. ..................................... 606/159
(58) Field of Classification Search .............. 606/15, 606/194, 159, 167, 170; 600/36
See application file for complete search history.

(56) References Cited

U.S. PATENT DOCUMENTS

| | | |
|---|---|---|
| 2,011,169 A | 8/1935 | Wappler |
| 2,028,635 A | 1/1936 | Wappler |
| 3,659,606 A | 5/1972 | Reimels |
| 3,764,427 A | 10/1973 | Reimels |
| 3,788,325 A | 1/1974 | Jacobsen |
| 4,052,980 A | 10/1977 | Grams et al. |
| 4,528,982 A | 7/1985 | Wellenstam |
| 4,655,217 A | 4/1987 | Reed |
| 5,011,489 A | 4/1991 | Salem |
| 5,013,312 A | 5/1991 | Parins et al. |
| 5,373,840 A | 12/1994 | Knighton |
| 5,395,384 A | 3/1995 | Duthoit |
| 5,522,827 A | 6/1996 | Combs et al. |
| 5,571,172 A | 11/1996 | Chin |
| 5,591,183 A | 1/1997 | Chin |
| 5,593,418 A | 1/1997 | Mollenauer |
| 5,601,581 A | 2/1997 | Fogarty et al. |
| 5,601,589 A | 2/1997 | Fogarty et al. |
| 5,607,441 A | 3/1997 | Sierocuk et al. |
| 5,653,722 A | 8/1997 | Kieturakis |
| 5,658,282 A | 8/1997 | Daw et al. |
| 5,667,480 A | 9/1997 | Knight et al. |

(Continued)

FOREIGN PATENT DOCUMENTS

WO WO 03/000139 1/2003

(Continued)

*Primary Examiner*—Todd E Manahan
*Assistant Examiner*—Eric Blatt

(57) ABSTRACT

A surgical instrument for harvesting vessels from the body includes an elongated shaft having distal and proximal ends and a plurality of lumens disposed therethrough. The shaft also includes a tip having a dissecting portion disposed at a distal end thereof and a cradle section. The tip is movable from a first position proximate the distal end of the shaft to at least one additional position distally further from the distal end of the shaft to expose the cradle section. The instrument also includes an endoscope disposed in one of the plurality of lumens and at least one additional surgical instrument disposed in one of the remaining lumens. Methods are disclosed for utilizing the surgical instrument.

31 Claims, 10 Drawing Sheets

U.S. PATENT DOCUMENTS

| | | |
|---|---|---|
| 5,676,636 A | 10/1997 | Chin |
| 5,690,668 A | 11/1997 | Fogarty et al. |
| 5,695,514 A | 12/1997 | Chin |
| 5,702,417 A | 12/1997 | Hermann |
| 5,707,382 A | 1/1998 | Sierocuk et al. |
| 5,716,325 A | 2/1998 | Bonutti |
| 5,722,934 A | 3/1998 | Knight et al. |
| 5,725,479 A | 3/1998 | Knight et al. |
| 5,730,748 A | 3/1998 | Fogarty et al. |
| 5,738,628 A | 4/1998 | Sierocuk et al. |
| 5,759,150 A | 6/1998 | Konou et al. |
| 5,762,604 A | 6/1998 | Kieturakis |
| 5,772,576 A | 6/1998 | Knighton et al. |
| 5,782,753 A | 7/1998 | DeFonzo et al. |
| 5,782,854 A | 7/1998 | Hermann |
| 5,797,946 A | 8/1998 | Chin |
| 5,797,947 A | 8/1998 | Mollenauer |
| 5,800,540 A | 9/1998 | Chin |
| 5,803,903 A | 9/1998 | Athas et al. |
| 5,814,059 A | 9/1998 | Hart et al. |
| 5,814,060 A | 9/1998 | Fogarty et al. |
| 5,817,013 A | 10/1998 | Ginn et al. |
| 5,823,946 A | 10/1998 | Chin |
| 5,827,318 A | 10/1998 | Bonutti |
| 5,836,945 A | 11/1998 | Perkins |
| D403,066 S | 12/1998 | DeFonzo |
| 5,843,104 A | 12/1998 | Samuels |
| 5,853,417 A | 12/1998 | Fogarty et al. |
| RE36,043 E | 1/1999 | Knighton |
| 5,871,496 A | 2/1999 | Ginn et al. |
| 5,873,889 A | 2/1999 | Chin |
| 5,876,413 A | 3/1999 | Fogarty et al. |
| 5,891,140 A | 4/1999 | Ginn et al. |
| 5,893,858 A | 4/1999 | Spitz |
| 5,893,866 A | 4/1999 | Hermann et al. |
| 5,895,353 A | 4/1999 | Lunsford et al. |
| 5,899,912 A | 5/1999 | Eaves, III |
| 5,899,913 A | 5/1999 | Fogarty et al. |
| 5,902,315 A | 5/1999 | DuBois |
| 5,902,316 A | 5/1999 | Mollenauer |
| 5,913,818 A | 6/1999 | Co et al. |
| 5,913,866 A | 6/1999 | Ginn et al. |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,138 A | 7/1999 | Knight et al. |
| 5,938,680 A | 8/1999 | Ginn |
| 5,944,734 A | 8/1999 | Hermann et al. |
| 5,951,584 A | 9/1999 | Hermann |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,979,452 A | 11/1999 | Fogarty et al. |
| 5,980,549 A | 11/1999 | Chin |
| 5,984,937 A | 11/1999 | Morse et al. |
| 5,993,384 A | 11/1999 | Lunsford et al. |
| 5,993,472 A | 11/1999 | Hermann et al. |
| 6,004,340 A | 12/1999 | Hermann et al. |
| 6,013,090 A | 1/2000 | Fogarty et al. |
| 6,019,771 A | 2/2000 | Bennett et al. |
| 6,022,313 A | 2/2000 | Ginn et al. |
| 6,030,396 A | 2/2000 | Samuels |
| 6,030,406 A | 2/2000 | Davis et al. |
| 6,036,713 A | 3/2000 | Kieturakis |
| 6,036,714 A | 3/2000 | Chin |
| 6,042,538 A | 3/2000 | Puskas |
| 6,051,013 A | 4/2000 | Mollenauer |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,080,102 A | 6/2000 | Konou et al. |
| 6,110,170 A | 8/2000 | Taylor et al. |
| 6,129,661 A | 10/2000 | Iafrati et al. |
| 6,139,489 A | 10/2000 | Wampler et al. |
| 6,143,008 A | 11/2000 | Eaves, III |
| 6,162,173 A | 12/2000 | Chin et al. |
| 6,174,313 B1 | 1/2001 | Bonutti |
| 6,193,651 B1 | 2/2001 | DeFonzo |
| 6,193,653 B1 | 2/2001 | Evans et al. |
| 6,196,968 B1 | 3/2001 | Rydin et al. |
| 6,203,557 B1 | 3/2001 | Chin |
| 6,203,559 B1 | 3/2001 | Davis et al. |
| 6,206,823 B1 | 3/2001 | Kolata et al. |
| 6,206,899 B1 | 3/2001 | Ginn |
| 6,228,024 B1 | 5/2001 | Co et al. |
| 6,240,924 B1 | 6/2001 | Fogarty et al. |
| 6,264,670 B1 | 7/2001 | Chin |
| 6,277,137 B1 | 8/2001 | Chin |
| 6,283,963 B1 | 9/2001 | Regula |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,375,665 B1 | 4/2002 | Nash et al. |
| 6,413,208 B1 | 7/2002 | Schollhorn et al. |
| 6,428,468 B1 | 8/2002 | Knighton et al. |
| 6,428,556 B1 | 8/2002 | Chin |
| 6,432,044 B1 | 8/2002 | Lunsford et al. |
| 6,436,116 B1 | 8/2002 | Spitz et al. |
| 6,436,118 B1 | 8/2002 | Kayan |
| 6,443,159 B1 | 9/2002 | Fogarty et al. |
| 6,443,970 B1 | 9/2002 | Schulze et al. |
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,454,784 B1 | 9/2002 | Mollenauer |
| 6,468,206 B1 | 10/2002 | Hipps et al. |
| 6,482,153 B1 | 11/2002 | Hipps et al. |
| 6,506,200 B1 | 1/2003 | Chin |
| 6,511,494 B1 | 1/2003 | Knighton et al. |
| 6,527,771 B1 | 3/2003 | Weadock et al. |
| 6,527,787 B1 | 3/2003 | Fogarty et al. |
| 6,551,335 B1 | 4/2003 | Bardeau et al. |
| 6,572,615 B2 | 6/2003 | Schulze et al. |
| 6,592,582 B2 | 7/2003 | Hess et al. |
| 6,592,604 B2 | 7/2003 | Hess et al. |
| 6,596,010 B1 | 7/2003 | Hermann et al. |
| 6,607,547 B1 | 8/2003 | Chin |
| 6,616,661 B2 | 9/2003 | Wellman et al. |
| 6,623,482 B2 | 9/2003 | Pendekanti et al. |
| 6,648,815 B2 | 11/2003 | Schoellhorn et al. |
| 6,652,521 B2 | 11/2003 | Schulze |
| 6,656,176 B2 | 12/2003 | Hess et al. |
| 6,660,016 B2 | 12/2003 | Lindsay |
| 2003/0195544 A1 | 10/2003 | Hess et al. |

FOREIGN PATENT DOCUMENTS

| | | |
|---|---|---|
| WO | WO 03/013365 | 2/2003 |
| WO | WO 03/013367 | 2/2003 |

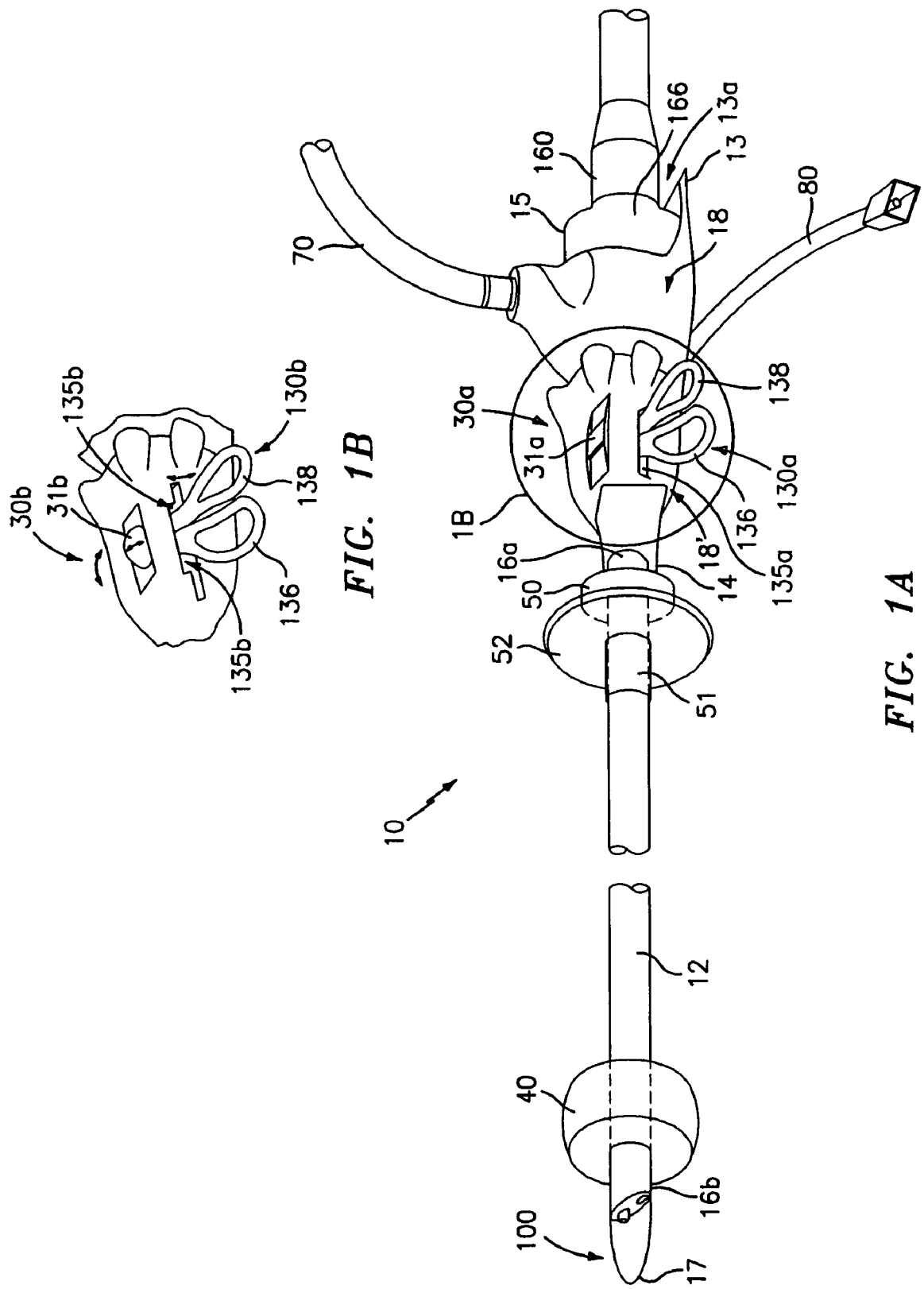

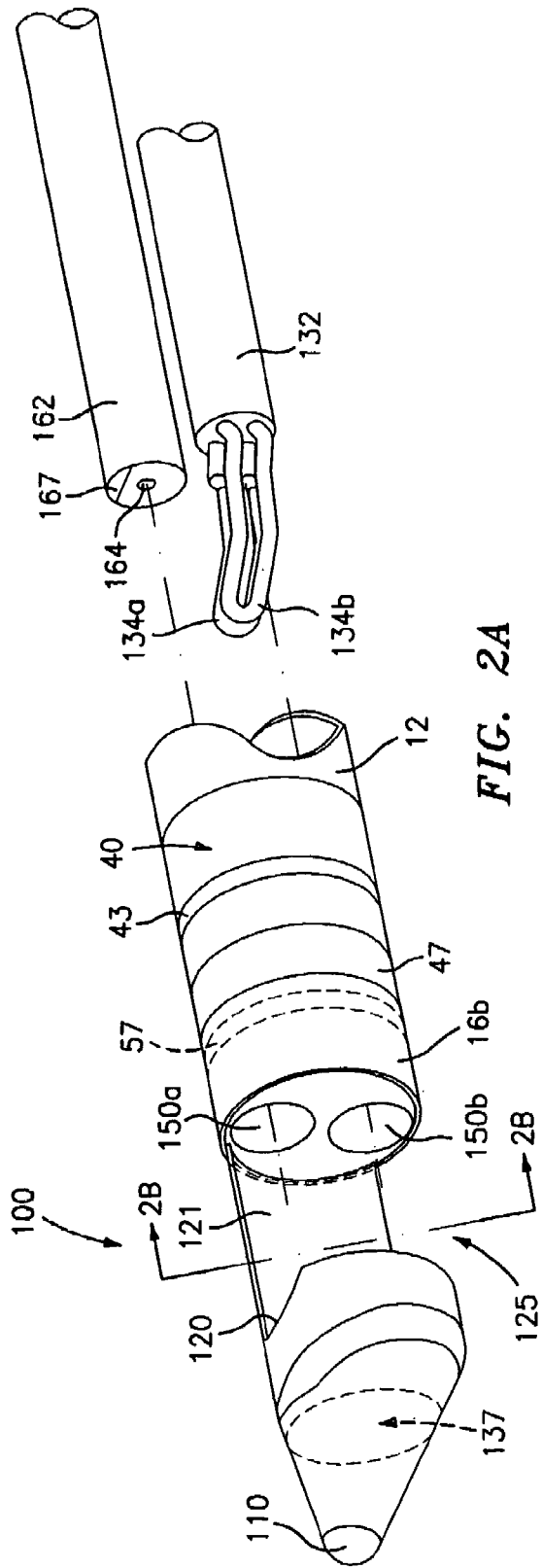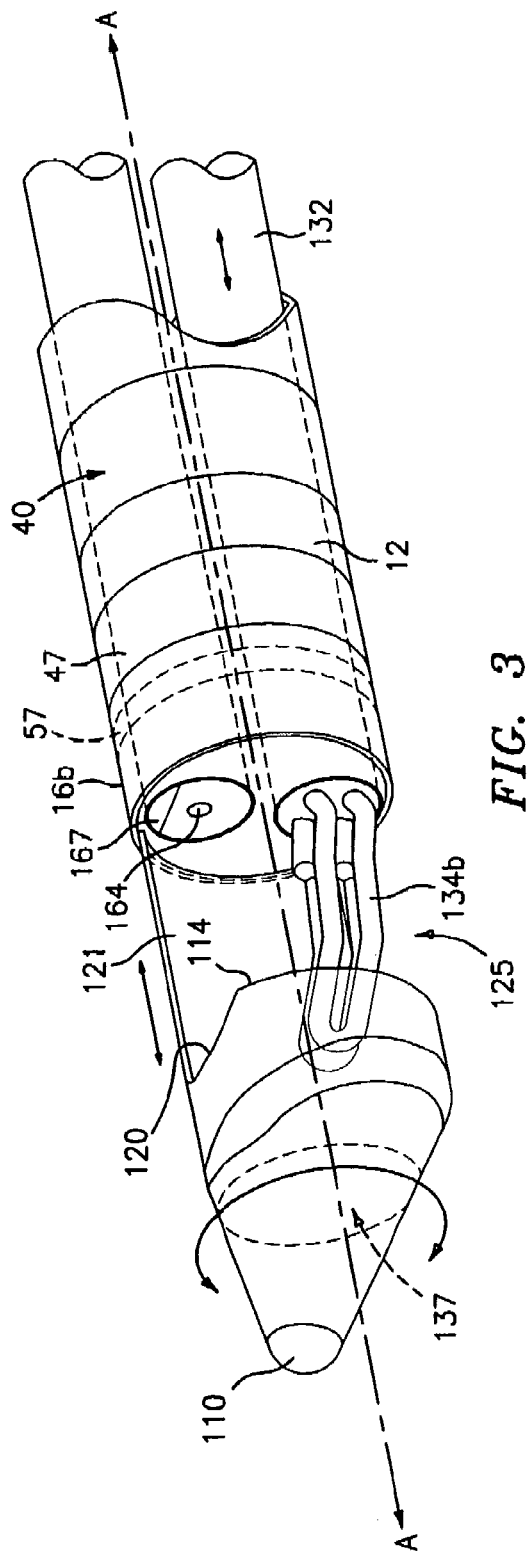
FIG. 2A
FIG. 3

CONDUIT HARVESTING INSTRUMENT AND METHOD

CROSS REFERENCE TO RELATED APPLICATIONS

This application is a continuation of PCT/US02/020450 filed on Jun. 26, 2002, which claims the benefit of and priority to U.S. Provisional Patent Application Ser. No. 60/301,059 entitled "CONDUIT HARVESTING INSTRUMENT AND METHOD" filed on Jun. 26, 2001 by Hanspeter R. Bayer, the entire contents of which are hereby incorporated by reference herein.

BACKGROUND

1. Field of the Disclosure

This present disclosure relates to instruments and methods for performing minimally invasive, laparoscopic or endoscopic surgical procedures. More particularly, the present disclosure relates to instruments and methods that are especially suitable for procedures that require or benefit from minimally invasive access to anatomical conduits or vessels for harvesting the same. The instrument is suitable for harvesting vessels from surrounding tissue for use in bypass procedures including, but not limited to, coronary artery bypass grafting (CABG) or reverse or in-situ femoral-popliteal or femoral-tibia peripheral bypass grafting.

2. Related Art

Coronary artery disease is often characterized by lesions or occlusions in the coronary arteries which may result in inadequate blood flow to the myocardium, or myocardial ischemia, which is typically responsible for such complications as angina pectoris, necrosis of cardiac tissue (myocardial infarction), and sudden death. In some cases, coronary artery disease may be treated by the use of drugs and/or by modifications in behavior and diet. In other cases, dilatation of coronary arteries may be achieved by such procedures as angioplasty, laser ablation, atherectomy, catheterization, and intravascular stents. Coronary bypass surgery is required when these methods of treatment cannot be used or have failed to clear the blocked artery.

Many surgical procedures have been developed to replace arteries that have come blocked by disease. For certain patients, a coronary artery bypass graft ("CABG") is the preferred form of treatment to relieve symptoms and the graft often increases life expectancy. A CABG procedure consists of direct anastomosis of a vessel segment to one or more of the coronary arteries. For example, a reversed segment of the saphenous vein may be grafted at one end to the ascending aorta as an arterial blood source and at the other end to a coronary artery at a point beyond the arterial occlusion.

Therefore and in order to perform a CABG procedure, a vessel must be harvested from the body and grafted into place on either side of the point of blockage. It is preferred to use a vein taken from the patient undergoing the bypass surgery to avoid and/or limit the chances of rejection by the body after grafting onto the aorta and coronary artery. The saphenous vein in the leg is often the most suitable candidate for use in coronary bypass surgery because the saphenous vein is typically 3 mm to 5 mm in diameter which is about the same size as a coronary artery. The cephalic vein in the arm is another suitable harvesting candidate for CABG procedures.

As can be appreciated, harvesting these conduits from the body often requires enormous skill and precision due to the delicate nature of the tissue structure. Various methods for harvesting vessels are known. For example, some surgeons typically cut the leg open and carefully dissect the surrounding tissue from the vein using dissecting scissors or tissue scraping instruments. Other surgeons make a series of incisions from the groin to the knee or the ankle leaving one or more skin bridges along the line of the incisions. The surgeon then literally strips the vein free from surrounding tissue using one or more surgical dissecting instruments.

While stripping the vein and removing the surround tissue, the surgeon will undoubtedly encounter the various tributary veins that feed into the saphenous vein. These tributaries must be ligated and separated from the vein prior to removal. As can be appreciated, ligating and separating these tributaries from the vein requires a high degree of skill and accuracy and is typically a very tedious procedure.

When the vein has been completely mobilized and the tributaries have been divided from the vein, the surgeon cuts the proximal and distal ends of the vein and removes the vein from the leg. Once removed, the vein is prepared for implantation into the graft site, and the long incision(s) made in the leg are stitched closed.

The procedures described above are often used to harvest veins for a femoral popliteal bypass or for the revascularization of the superior mesenteric artery which supplies blood to the abdominal cavity and intestines. In addition, the above-described procedures can be used to harvest the umbilical vein or to harvest veins for femoral-tibial, femora-peroneal, aorto-femoral, and iliac-femoral bypass operations and any other bypass operation.

As can be appreciated from the above descriptions, the harvesting of vessels can be very traumatic and is often the most troublesome part of the bypass operation. Moreover, the incisions, especially the long ones, created in the leg or arm to harvest the vessel tend to heal slowly and are often very painful.

Over the last several years, minimally invasive, for example endoscopic tools and methods have been developed for harvesting vessels which are less intrusive and less traumatic. For example, with one known technique, the surgeon makes a few small incisions in the leg and inserts one or more elongated surgical instruments, e.g., forceps, scissors, clip appliers, staplers, etc., into the incision and carefully manipulates the instruments while viewing the operating area through an endoscopic or laparoscope. These techniques are often referred to as endoscopic, laparoscopic, minimally invasive, or video-assisted surgery. References to endoscopic surgery and endoscopes below is intended to encompass all these fields, and the exemplary operations described below with reference to endoscopes can also be accomplished with laparoscopes, gastroscopes, and any other imaging devices which may be conveniently used.

Other minimally invasive procedures for vein harvesting are also known. For example, soviet patent number SU 1371689 teaches a vessel removal procedure which utilizes an endoscope having a lumen extending therethrough. In this procedure, the saphenous vein is grasped and held with a grasper which is introduced through the lumen of the endoscope. After connective tissue has been dissected from around the vein, a length of the vein is ligated, transected and removed from the lower limb of the patient through the lumen of the endoscope. U.S. Pat. No. 5,373,840 discloses a method for harvesting the saphenous vein which also utilizes an endoscope having a lumen disposed therethrough.

Other known techniques employ balloons which are inflated to create a working cavity or tunnel along the length of the vein. For example, U.S. Pat. No. 5,601,581 describes a method of vein harvesting which utilizes an everted balloon to assist in dissecting the harvested vein. The balloon is stored inside a cannula which is inserted through one of the small incisions in the leg and inflated so that it everts out the end of the cannula and forces its way along the vein to create a tunnel.

Typically, many of the above-described techniques require the surgeon to insert different instruments through the working lumen of the endoscope to dissect tissue and to separate vessel tributaries. As can be appreciated, this simply adds to the overall complexity of the operation since it requires the repeated exchange of surgical instruments through the working lumen to perform the different tasks associated with blunt dissection and removal of the vessel tributaries.

Thus, a need exists to develop an endoscopic vessel harvesting instrument and method for harvesting vessels which allows the operator to both dissect surrounding tissue from the vein and selectively manipulate, grasp and separate vessel tributaries from the vein without removing and/or exchanging instruments through the working lumen.

SUMMARY

The present disclosure relates to a surgical instrument for harvesting vessels which includes an elongated shaft having distal and proximal ends and a plurality of lumens disposed through the shaft. The shaft preferably includes a tip having a blunt dissecting portion disposed at a distal end of the shaft and a cradle section disposed between the blunt dissecting portion and the distal end of the shaft. Preferably, the tip is selectively movable from a first dissecting position wherein the tip is proximate the distal end of the shaft to an expanded position distally further from the distal end of the shaft to expose the cradle section. The instrument also includes an endoscope disposed in one of the plurality of lumens and at least one additional surgical instrument disposed in one of the remaining lumens.

Preferably, the dissecting portion is transparent and/or conical in dimension to facilitate blunt dissection of surrounding tissue from the vessel. In one embodiment, the tip is extendable along a longitudinal axis defined through the shaft to expose the cradle section. Advantageously, the cradle section includes a notched portion to facilitate manipulation, orientation and positioning and securement of a vessel tributary and to facilitate its ligation and/or separation from the main conduit vessel. The tip and/or the cradle section is preferably rotatable about the endoscope to assist in the orientation of the cradle section for and during manipulation and separation of the vessel tributaries 360° about the vessel. The tip and/or the cradle section can also be selectively rotatable about the axis of the shaft Additional instruments which can be disposed through one or more of the remaining lumens in the shaft can be selected from the group consisting of: ligating instruments, bipolar shears, ultrasonic shears, clip appliers, coagulating instruments, cutting instruments, vessel sealing instruments, vessel graspers, irrigation instruments, insufflators, suction instruments and combinations of the same. It is envisioned that the additional instruments may be selectively extendable, retractable and/or rotatable relative to the instrument, shaft or endoscope to facilitate operation thereof.

In one embodiment, the additional instrument is an electrosurgical ligating instrument which is remotely operated by an actuator, e.g., a trigger located adjacent the proximal end of the shaft or an actuator remotely located for remote activation and/or manipulation of the trigger or the actuator. Preferably, the trigger or actuator allows the operator to selectively manipulate (i.e., extend and/or rotate) and activate the ligating instrument as needed during ligation and/or separation of the vessel tributaries and/or removal of the vessel from the body.

In another embodiment, the shaft, preferably a distal portion thereof, includes a balloon disposed about the outer periphery thereof and which is selectively inflatable and/or deflatable. The balloon allows the operator to grossly dissect surrounding tissue away from the vessel and create and/or maintain a working space between the vessel and the tissue. The working space may be insufflated as needed during the harvesting procedure to facilitate visualization and removal of the vessel.

Another embodiment of the present disclosure is a surgical instrument for dissecting a vessel from surrounding tissue which includes a housing and an elongated shaft preferably attached to the housing. The shaft includes a plurality of lumens disposed at least partially therethrough. A blunt tip is disposed at a distal end of the shaft and is selectively movable by an actuator mounted to the housing. The actuator allows the operator to extend the tip from a first dissecting position wherein the tip is positioned proximate the distal end of the shaft (i.e., positioned to separate surrounding tissue from the vessel) to at least one additional position distally further from the distal end of the shaft to expose a cradle section. An endoscope is disposed in at least one of the lumens for visualization purposes and one or more additional surgical instrument(s) (preferably selected from the list mentioned above) is disposed in one or more of the remaining lumens.

The actuator can include a ball-like mechanism which allows the operator to selectively extend and/or rotate the blunt tip, cradle section and/or shaft for manipulating, positioning and separating vessel tributaries.

Another embodiment of the present disclosure includes an endoscopic vessel harvesting instrument having a housing with proximal and distal ends and an elongated shaft attached to the housing, preferably its distal end. The shaft includes a tip integral with or slidingly attached to a portion of the instrument and operative at or adjacent to the distal end of the shaft. The shaft also includes a plurality of lumens disposed at least partially through and in communication with the distal end of the shaft. Preferably each of the lumens is dimensioned to accommodate one of a plurality of surgical instruments selected from the group consisting of: endoscopes, ligating instruments, bipolar shears, ultrasonic shears, clip appliers, coagulating instruments, cutting instruments, vessel sealing instruments, insufflators, vessel graspers, irrigation instruments, suction instruments and combinations of the same. The endoscopic vessel harvesting instrument can include a balloon attached to an outer periphery of the shaft and an actuator engagable with or engaged to one of the plurality of instruments for selectively operating and/or manipulating one or more of the plurality of instruments relative to the shaft, axis or endoscope. An actuator is disposed on the shaft, in the shaft housing or in the base housing for selectively operating and/or manipulating the tip and/or the cradle section relative to the shaft, axis and/or endoscope. An inflation port can also be included with the vessel harvesting instrument for selectively inflating the balloon for grossly or otherwise dissecting or distancing surrounding tissue.

The present invention also relates to a method for harvesting a vessel from surrounding tissue. The method includes the steps of: providing a surgical instrument having a housing with distal and proximal ends. The housing can have an elongated shaft attached at a distal end thereof which includes a blunt tip and a plurality of lumens disposed therethrough. Preferably, one of the lumens is dimensioned to accommodate an endoscope and at least one of the remaining plurality of lumens is dimensioned to accommodate an additional surgical instrument selected from the group consisting of: ligating instruments, bipolar instruments, ultrasonic instruments, clip appliers, coagulating instrument, cutting instruments, vessel sealing instruments, insufflators, vessel graspers, irrigation instruments, suction instruments and/or combinations of the same. The tip is selectively movable to expose a cradle section between the tip and a distal end of the shaft.

The method can include the steps of: inserting the instrument into an incision in the body (either directly or through a cannula); advancing the instrument through the incision and along the vessel; utilizing the endoscope to view the internal working space and the blunt tip to dissect surrounding tissue from the vessel; selectively extending the blunt tip to expose the cradle section to position therein vessel tributaries for treatment (i.e., grasping, separating, dividing, ligating, occluding, cutting, etc.) by the additional one or more surgical instruments; repeating the advancing and extending steps as needed to clear surrounding tissue from the vessel and treat vessel tributaries; and removing the vessel from the body.

Before or after the extending step, the method may include the step of: rotating the blunt tip, and/or the cradle section to position tributaries therein for treatment. The shaft of the providing step may include a balloon attached to the outer periphery thereof and after the advancing step, the method may include the step of: selectively inflating the balloon to further dissect surrounding tissue from the vessel to create a space between the vessel and surrounding tissue. Preferably, after the inflating step, the method includes the step of: insufflating the space between the vessel and surrounding tissue with a gas.

The present disclosure also relates to a method for harvesting a vessel from surrounding tissue which includes the steps of: providing a surgical dissector having a housing with distal and proximal ends. The housing includes an elongated shaft attached at a distal end of the housing which has a blunt tip and at least one lumen disposed therein for housing an endoscope. The tip is selectively extendable from the shaft to expose a cradle section for positioning and treating tributaries of the vessel.

The method can also include the steps of: inserting the instrument through an incision in the body; advancing the instrument through the incision and along the vessel utilizing the endoscope to view and/or the blunt tip to dissect surrounding tissue from the vessel; selectively extending the blunt tip to expose the cradle section and position a vessel tributary; sealing and separating a portion of the tributary from the vessel; repeating the advancing, extending and treating steps as needed to clear surrounding tissue from the vessel and/or seal or separate additional vessel tributaries; and removing the vessel from the body. Preferably, the advancing step is effected with the blunt tip retracted to reduce exposure of the cradle section. After the extending step, the method can further include the step of: rotating the cradle section to position tributaries for treatment.

Other methods for harvesting a vessel from surrounding tissue include the steps of: providing a surgical instrument having a housing including distal and proximal ends. The housing has an elongated shaft attached at a distal end thereof which includes a blunt tip, a cradle section and a plurality of lumens disposed therethrough. One of the lumens is dimensioned to accommodate an endoscope, and at least one of the remaining plurality of lumens is dimensioned to accommodate one of a plurality of additional surgical instruments selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same. Preferably, the tip is selectively movable to expose the cradle section, and the cradle section is located between the tip and a distal end of the shaft.

The method also includes the steps of inserting the instrument into an incision in the body; advancing the instrument distally through the incision and along the vessel with the cradle section unexposed; with the cradle section unexposed, utilizing the endoscope to view and the blunt tip and/or the unexposed cradle section to dissect surrounding tissue from the vessel and form an operating cavity; selectively extending the blunt tip to expose the cradle section; withdrawing the instrument in a proximal direction through the operating cavity and utilizing the exposed cradle section to position vessel tributaries for treatment by one of the plurality of additional surgical instruments; and treating the vessel tributaries by use of the one of the plurality of surgical instruments.

Still another method for harvesting a vessel from surrounding tissue, includes the steps of: providing a surgical dissector having a housing including distal and proximal ends. The housing has an elongated shaft extending from at a distal end of the housing. The shaft includes a blunt tip and at least one lumen disposed therethrough for housing an endoscope. The blunt tip is selectively extendable from the shaft to expose a cradle section for positioning vessel tributaries.

The method also includes the step of: inserting the instrument into an incision in the body; advancing the instrument through the incision and along the vessel utilizing the endoscope to view and the blunt tip to dissect surrounding tissue from the vessel; selectively extending the blunt tip to expose the cradle section and position a vessel tributary; and separating the tributary from the vessel.

The method can comprise effective dissection while moving the instrument distally into and through the incision and along a main vessel and, with the blunt tip retracted, dissecting tissue from the main vessel (and tributary vessel) and with the blunt tip still retracted, withdrawing the instrument in the proximal direction; extending the blunt tip distally away from the shaft to expose the cradle section; and advancing the instrument in the distal direction with the blunt tip extended and cradling a tributary vessel and treating it with the additional one or more surgical instrument housed in one or more of the lumens. The treating step can include ligating and transecting one or more tributary vessel to free the main vessel from its tributary vessel to enable a section of the main vessel to be withdrawn from the incision.

In accordance with another method of the present disclosure, the method for harvesting can include the steps of: A method for harvesting a vessel from surrounding tissue, comprising the step of: providing a surgical instrument having:

a housing including distal and proximal ends, the housing having an elongated shaft attached thereto and extending from a distal end thereof, the shaft including a blunt tip, a cradle section and a plurality of lumens disposed through at least portions of the shaft, one of the lumens being dimensioned to accommodate an endoscope, and at least one of the remaining plurality of lumens being dimensioned to accommodate one of a plurality of additional surgical instruments selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same;

the tip being selectively distally extendible from a retracted position to expose the cradle section, the cradle section being located between the tip and a distal end of the shaft.

The method also includes the steps of:
inserting the instrument into an incision in the body;
advancing the instrument distally through the incision and along the vessel with the tip in a retracted position with the cradle section substantially unexposed;
utilizing the endoscope to view and the blunt tip to dissect surrounding tissue from the vessel to form an operating cavity;
retracting the instrument in a proximal direction toward the incision;
extending the blunt tip to expose the cradle section;
re-advancing the instrument distally through the incision and along the vessel with the cradle section exposed;
utilizing the exposed cradle section to successively position respective vessel tributaries therein; and
treating the successive cradled vessel tributaries by use of the one of the plurality of additional surgical instruments.

BRIEF DESCRIPTION OF THE DRAWINGS

Other objects and features of the present disclosure will become apparent from the following detailed description considered in connection with the accompanied drawings. It should be understood, however, that the drawings are designed for the purpose of illustration only and not as a definition of the limits of the invention.

An illustrative embodiment of the subject surgical instrument and method are described herein with reference to the drawings wherein:

FIG. 1A is a perspective view of an endoscopic instrument for harvesting vessels according to the present disclosure which includes an elongated shaft having a plurality of lumens disposed therethrough and a blunt tip located at a distal end thereof;

FIG. 1B is an enlarged, isolated view of a ball-like actuator which moves the blunt tip as needed for blunt dissection and ligation purposes and a trigger mechanism which moves and actuates a ligation instrument;

FIG. 2A is an enlarged, exploded perspective view with portions removed and portions broken away, of the blunt tip of the harvesting instrument of FIG. 1 having a movable cradle section for handling vessel tributaries and showing an endoscope for viewing the surgical area and an instrument for ligating and cutting vessel tributaries;

FIG. 3 is an enlarged, perspective view with portions removed and portions broken away, of the harvesting instrument of FIG. 1 showing the endoscope and the ligation and cutting instrument housed therein and illustrating the rotational and axial capabilities of the blunt tip, shaft and cradle portions relative to the endoscope;

DETAILED DESCRIPTION

Figure 2B:
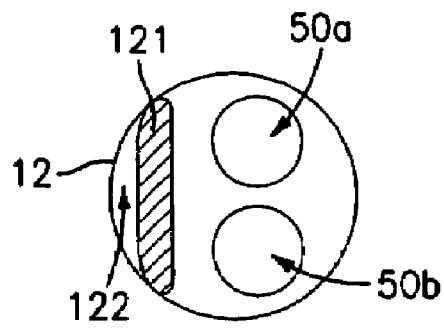
FIG. 2B is a front view of an alternate embodiment of the elongated shaft showing a cradle arm of the cradle section disposed in of a self-enclosed recess disposed radially inward of the outer periphery of the elongated shaft.
Figure 2C:
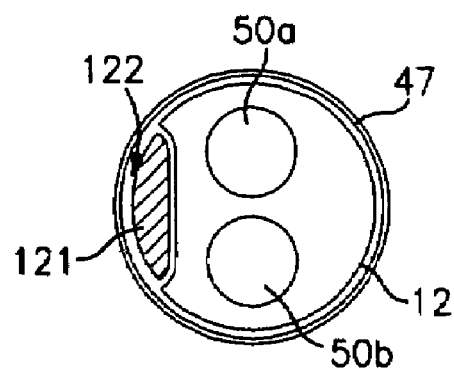
FIG. 2C is a front view of an alternate embodiment of the elongated shaft showing the cradle arm of the cradle section disposed within a recess formed within the outer periphery of the elongated shaft and an outer tube which surrounds the shaft and the cradle arm to slidingly maintain the cradle arm within the slot.

Referring now to FIGS. 1A-4, there is disclosed one embodiment of an endoscopic vessel harvesting instrument 10 that can be employed for harvesting vessels 200 (FIG. 5) for use, e.g., in bypass procedures, in particular, coronary bypass procedures. Harvesting instrument 10 includes a proximal end 15, a distal end 17 and an elongated shaft 12 disposed therebetween, but not necessarily in direct communication with such ends 15 and 17. For the purposes herein, it is understood that FIG. 1A discloses one embodiment of the presently disclosed instrument. As described in more detail below, it is envisioned that the instrument may include a base housing which is integral with or attachable to a shaft housing and a shaft which is integral with or attachable to the shaft housing. In such instances, what is commonly termed the "proximal end" may change depending upon whether a single, integral, base housing is utilized or a combination base housing and shaft housing is utilized.

Elongated shaft 12 includes proximal and distal ends 16a and 16b, respectively, and is preferably dimensioned to fit in a 12 mm or 15 mm trocar. A base housing 18 is disposed at or near the proximal end 15 of the instrument 10 and a preferably transparent, preferably conical blunt dissection tip 100 is extendibly disposed at the distal end 17 of the instrument 10. The base housing 18 is designed to accommodate various surgical instruments (described in detail below) as well as facilitate remote operation of proximal portions of the harvesting instrument 10 and its lumen-housed instruments directly or indirectly by the surgeon outside the operating cavity. For the purposes herein, housing 18 may be integral with shaft housing 18' to define a single housing 18 or, alternatively, the shaft housing 18' may be removably engaged with the housing 18.

Figure 11:
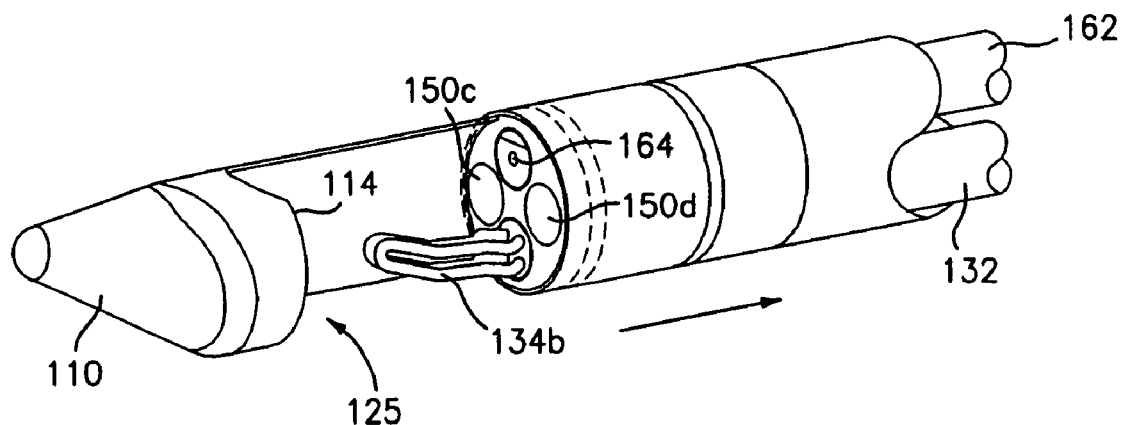
FIG. 11 is a perspective view of another embodiment of the present disclosure wherein the shaft includes a plurality of the lumens for housing additional surgical instruments therein.

Elongated shaft 12 is dimensioned to fit through a cannula or trocar port 51 which can be inserted by the surgeon into an incision at the onset of the harvesting operation. Shaft 12 communicates with, extends from and is attached to a shaft housing 18' which is selectively engaged with the base housing 18. The proximal end of the shaft 16a can also be selectively engageable with the shaft housing 18'. The shaft 12 also includes plurality of lumens, for example, 150a-150d (FIG. 11) extending or at least partially disposed therein or at least partially therethrough for housing various surgical instruments used in connection with harvesting the vessel 200. Preferably, the lumens can accommodate instruments approximately 5 mm to 7 mm in width. For example and as best illustrated in FIGS. 2 and 3, the shaft 12 includes a first lumen 150a which can house an endoscope 162 for observing or visualizing the operating cavity 400 (FIG. 5) during dissection of the surrounding tissue 300 and ligation and/or transection of the tributary branches of the vessels (explained in more detail below with respect to the operation of the instrument). Preferably, endoscope 162 is constructed to be part of instrument 10. Shaft 12 also includes a second lumen 150b for housing an additional surgical instrument, here a ligating/cutting instrument 132, hereinafter sometimes referred to simply as a ligating or ligation instrument, such as the TRIMAX™ instrument manufactured by United States Surgical, a division of Tyco Healthcare Group LP of Norwalk, Conn.

Figure 7:
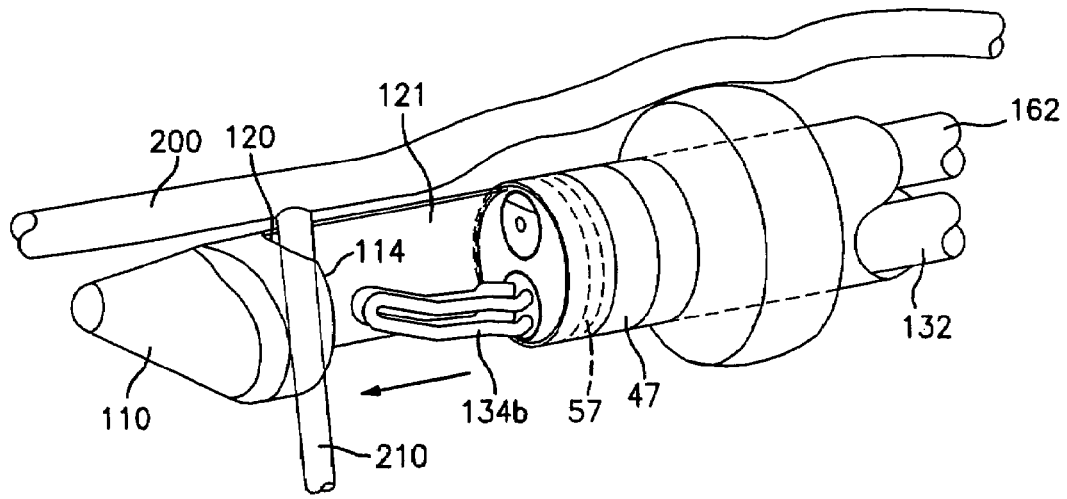
FIG. 7 is a perspective view of the harvesting instrument showing the blunt tip in an extended position and showing the ligation instrument being extended toward the cradled vessel tributary.

Preferably, ligation instrument 132 is constructed as part of instrument 10 and preferably ligation instrument 132 is selectively axially extendable from the lumen as best shown in FIGS. 3 and 7 and as described in more detail below. Other suitable desired instruments may be housed in lumens 150a and/or 150b, and additional instruments may also be housed within one or more additional lumens, e.g., 150c, 150d which may be utilized for dissection and/or ligation, cauterization or other purposes (see FIGS. 10 and 11). Ligating instrument 132 can, and preferably does include a mechanical or electromechanical edge for cutting or transecting vessel tributaries 210. Each lumen, e.g., 150a, preferably is dimensioned and/or includes or has an associated gasket, o-ring or other sealing component, e.g., grease, to maintain a tight, gaseous seal between the lumen-housed instruments and the inner periphery of the housed instrument's lumen, e.g., 150a.

Shaft 12 extends distally from a distal end 14 of the shaft housing 18' and is dimensioned to sealingly slide (see FIG. 1A) and/or rotate within the trocar port 51 or a trocar during blunt dissection as described in more detail below. It is envisioned that the shaft 12 may be integral with, pass through or be selectively engageable with shaft housing 18' and/or the base housing 18 depending upon the particular configurations or purpose(s) of instruments 10. A balloon-like seal 52 can be coupled to the trocar port 51 for disposition inside and against a minimally invasive incision and to cooperate with a sponge-like stop member 50 disposed at a proximal end 16a of the shaft 12 exterior of and against the incision to limit or regulate the distal movement of the shaft 12 (and/or seal the shaft) within the trocar port 51, and/or within the minimally invasive incision through which the instrument is at least initially employed.

As can be appreciated, the position of balloon seal 52 and stop member 50 and/or the length of the shaft 12 may be sized or adjusted prior to the harvesting operation such that the position of the stop member 50 on the shaft 12 corresponds to the desired length of vessel 200 to be harvested, i.e., when the stop member 50 abuts against the balloon seal 52, the surgeon has successfully dissected the appropriate amount of surrounding tissue 300 and removed enough tributary branches 210 from the vessel 200 for safe and facile removal of the desired length of the vessel 200 from the operating cavity. Moreover and as mentioned above, differently-sized shafts 12 may be selectively engaged with the shaft housing 18' to ensure that the proper length of vessel 200 will be harvested.

Base housing 18 can include a proximal end 13 which includes a cavity 13a for housing a camera 166 which electronically couples to the endoscope 162 for viewing tissue, operating cavity 400, vessel 200 and/or vessel tributaries 210. Endoscope 162 may also include a strain relief member 160 which protects the endoscope from damage during use. It is envisioned that the camera 166 may be connected to a monitor (not shown) to enhance display of operating cavity 400, etc. Base housing 18 also includes an inflation port 70 which by suitable channel or port means is in communication with the balloon 40 and which allows the user to selectively inflate and deflate a balloon 40 disposed along the outer periphery of shaft 12 preferably towards the distal end, to grossly dissect surrounding tissue 300 from vessel 200 (see FIGS. 4 and 5). Selective inflation of the balloon 40 also forms the operating cavity 400 which may be insufflated with a fluid or gas to facilitate viewing of tissue, operating cavity 400, vessel 200 and vessel tributary branches 210. Preferably, balloon 40 is seated within a recess 43 disposed about the outer periphery of shaft 12. Incorporating the balloon 40 is optional and other known cooperative mechanisms for grossly or otherwise dissecting the operating area are also envisioned.

The shaft housing 18' includes an actuator, e.g., 30a or 30b and an actuator, for example, a trigger mechanism 130a or 130b (FIG. 1B) which controls the various instruments used for dissection. Actuator 30a (or 30b) allows the user to selectively extend and retract tip 100 as needed for blunt dissection of the vessel 200 from the surrounding tissue 300 and for cradling, orienting and facilitating ligation, transection and/or removal of tributary branches 210. In the embodiment of FIG. 1A, the actuator 30a includes a toggle 31a which simply permits axial translation of the tip 100 as needed for cradling, blunt dissection and separation of vessel tributaries 210. FIG. 1B shows an alternative embodiment of the actuator, 30b, which includes a ball-like toggle member 31b which allows both axial translation and rotation of the shaft 12 and tip 100 including cradle section 114 (see FIG. 4.) as needed 360° for blunt dissection of tissue and ligation and separation of vessel tributaries 210.

Trigger mechanism 130a (130b) allow the user to selectively activate the electrosurgical ligating instrument 132 for ligating and cutting the tributary branches 210 from the vessel 200. Trigger 130a or 130b is electrically coupled to an electrosurgical generator (not shown) by a cable 80 which supplies electrosurgical energy to the ligating instrument 132. One embodiment of the trigger 130a, as best illustrated in FIGS. 1A and 3, includes first and second handles 136 and 138, respectively, which are axially moved within a slot 135a disposed in the shaft housing 18' to extend (or retract) the ligating instrument distally. Simultaneously (or previously or subsequently) the handles 136 and 138 may be actuated, i.e., "squeezed", to move a pair of electrosurgical jaw members 134a and 134b relative to one another to grasp and ligate a vessel tributary 210. Electrosurgical energy is applied to the jaw members 134a and 134b to ligate, and a knife blade or energy is applied between the ligated portions to cut the vessel tributary 210 from the vessel 200. It is envisioned that the electrosurgical ligating instrument 132 may be activated upon initial "squeezing" of either or both two jaw members 134a and 134b or by a separate electrical switch, e.g., a "footswitch", depending upon a particular purpose. It is also envisioned that the "squeezing" of the handles 136 and 138 may perform a dual function, e.g., operate the grasping and cutting components of the TRIMAX™. For example, the initial squeeze of the handles 136 and 138 cooperate to grasp and ligate in two separate areas the vessel 200 between the ligated portions and continued squeezing reciprocates a knife to cut the vessel 200. An electrosurgical actuator, i.e., switch (not shown), may also be employed on the trigger assembly 130a. It is envisioned that an actuator (not shown) may be included with the housing 18 and/or the shaft housing 18' to rotate the shaft 12 relative to the endoscope or about the longitudinal.

An alternate embodiment of trigger mechanism 130a is adapted to permit selective axial translation and/or rotation of the ligating instrument 132 as needed for approximating, positioning, ligating and cutting the vessel tributaries 210. For example, FIG. 1B shows an elongated and vertically spaced slot 135b which permits the user to axially translate the handles 136 and 138 to extend or retract the jaw members 134a and 134b and also permits the user to simultaneously or otherwise rotate the handles 136 and 138 to rotate the ligating instrument 132 as needed for separation of the vessel tributaries 210. More detail with respect to this aspect of operation of the ligating instrument 132 is explained below with respect to FIGS. 5-9.

It is envisioned that additional surgical instruments may be utilized with the present disclosure which may be controlled from the shaft housing 18' (or base housing 18) or separate remote control box (not shown). For example, graspers, irrigation devices, e.g., nozzles and sprayers (see FIG. 10), suction instruments, clip appliers, bipolar or monopolar instruments, scissors, insufflators, vessel sealing instruments, etc., may incorporated with the instrument 10 and operated/controlled from shaft housing 18' a separate and/or remote housing or control box (not shown). Lumens can be provided through the shaft 12 and/or tip 100 to accommodate one or more of these additional instruments (see FIG. 11).

As mentioned above, the distal end 16b of the shaft 12 includes an eccentrically, conically-shaped, blunt tip 100 which is preferably transparent for visualization of the working cavity 400. It is envisioned that the presently disclosed design of the tip 100 provides the surgeon with the following advantages: 1) the blunt-like dimensions of the tip 100 enable the surgeon to dissect tissue 300 away from the vessel 200 without causing trauma to the vessel 200 or the surrounding tissue 300; 2) the transparent aspects of the tip 100 provide clear visualization of the surrounding operating cavity 400 with the endoscope 162 during blunt dissection of the vessel 200, during cradling, orientation and ligation of the tributary branches 210; and 3) the tip 100 is selectively extendable and retractable to expose the cradle section for positioning, cradling, grasping, trapping, engulfing and/or localizing vessel tributary branches 210 which need to be separated from the vessel 200 prior to removal. The eccentric design and location of the nose of the tip 100 close to the outer periphery of blunt tip 100 allows the nose to dissect tissue 300 that is located close to the vessel 100. Rotation of the instrument 10 about vessel 1000 permits close dissection 360° about the vessel.

Figure 4:
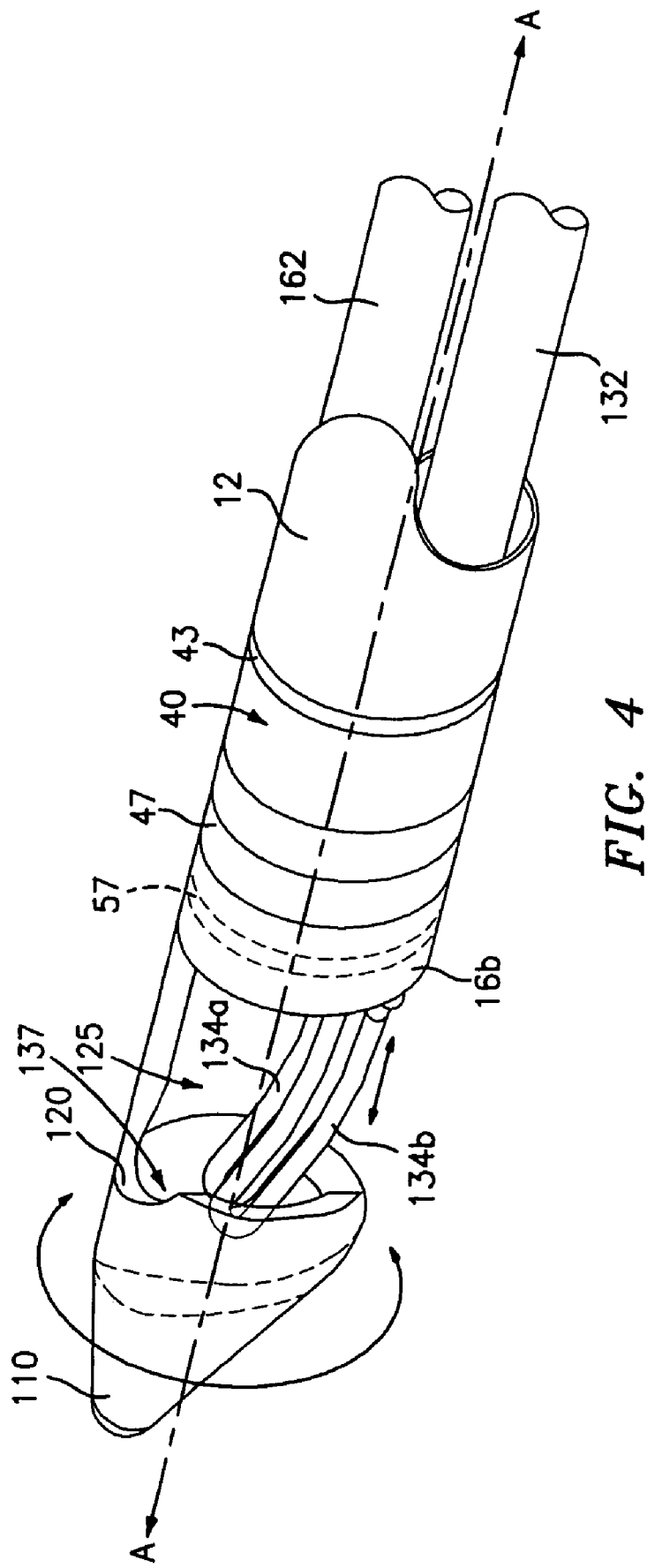
FIG. 4 is a rear perspective view of the harvesting instrument of FIG. 1.
Figure 5:
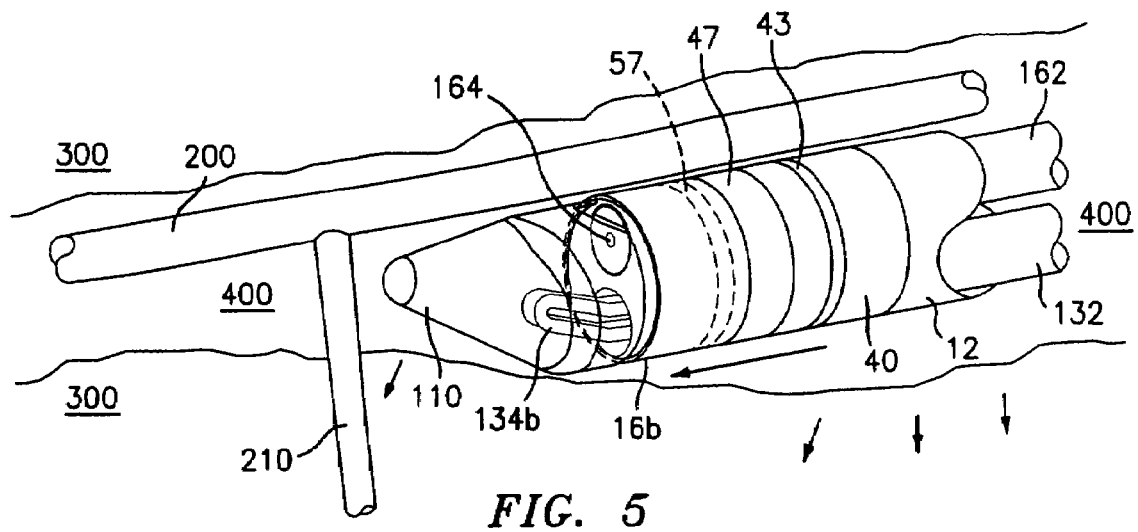
FIG. 5 is a perspective view of the harvesting instrument with the blunt tip in a retracted position for blunt dissection of the main vessel from the surrounding tissue.

As shown best in FIG. 3, the blunt tip 100 is preferably aligned with and rotatable about the endoscope 162 to provide optimal visualization of the blunt tip 100 in the operating cavity as the blunt tip 100 engages tissue 300 and vessel tributary branches 210. In one preferred embodiment, the blunt tip is rotatable but is continuously axially aligned with the endoscope to provide optimal viewing of the vessels, operating cavity and cutting cavity. It is also envisioned that, blunt tip 100 can be selectively extended or retracted along and/or rotated about a longitudinal axis "A" defined through shaft 12, as best illustrated in FIGS. 3 and 4. As can be appreciated, this gives the surgeon even more control during dissection and while cradling and positioning vessel tributaries 210. Moreover, blunt tip 100 includes a notched portion 120 which is dimensioned to both facilitate cradling, orientation and positioning or grasping of vessel tributaries 210 and to likewise facilitate securing vessel tributaries 210 during ligation (see FIGS. 6-9).

Figure 6:
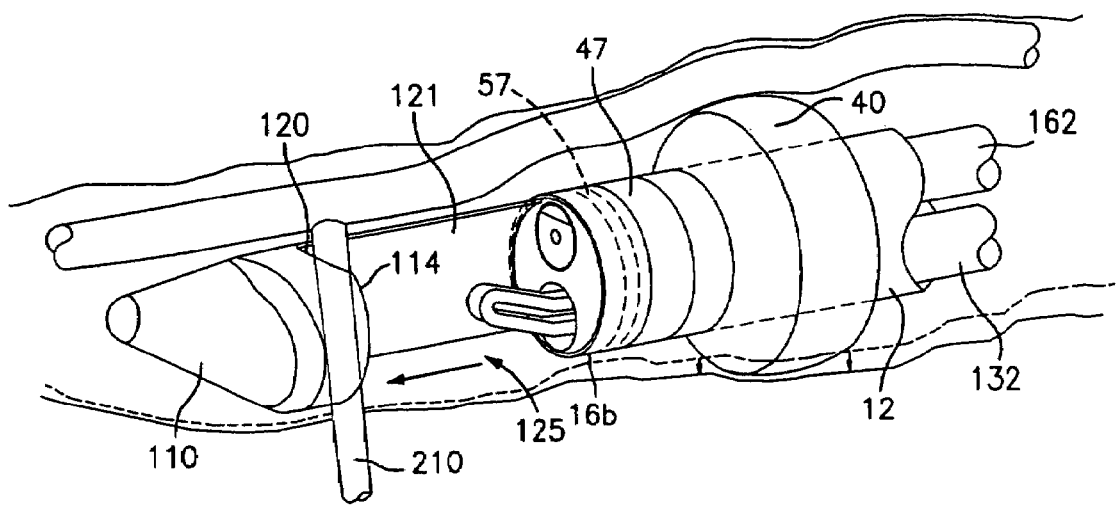
FIG. 6 is a perspective view of the harvesting instrument showing the blunt tip in an extended position to position a vessel tributary and showing a dissection balloon being inflated for grossly dissecting the surrounding tissue from the vessel.

Turning now to the operation of the harvesting instrument 10 as best seen in FIGS. 5-9, the instrument 10 is initially introduced into an incision though a trocar or cannular port 51 with the blunt tip 100 disposed in a retracted, preferably fully retracted, position. Endoscope 162 is retracted, i.e., not extended beyond the distal end 16b of shaft 12, and ligating instrument 132 is preferably at least partially retracted. The tissue 300 surrounding the vessel 200 to be harvested is initially dissected and cleared utilizing the blunt tip 100 as the instrument 10 is manually inserted and manipulated within the port 51. It is envisioned that the surgeon delicately dissects the surrounding tissue 300 from the vessel 200 by manipulating and rotating instrument 10, shaft 12, tip 100 and/or cradle section 114 either manually or utilizing the ball-like slide 31b (or other type of actuator) identified in FIG. 1B. Once the portion of the vessel 200 is dissected from the immediate surrounding tissue 300, the surgeon then selectively inflates the balloon 40 to grossly dissect the surrounding tissue 300 from the vessel 200 (FIG. 6). This creates and helps to maintain an operating cavity 400 between the vessel 200 and the surrounding tissue 300 thereby exposing attached vessel tributaries 210.

As can be appreciated, the transparency or transparent aspects of the tip 100 allow clear visualization of the operating cavity 400, the vessel 200 and vessel branches 210 through the tip 100. At this point, the surgeon may insufflate the cavity 400 through, e.g., lumen 150d, with a gas utilizing an insufflation port (not shown) which may be coupled to the trocar port 51 or located independently within operating cavity 400. As mentioned above, the balloon-like seal 52 (FIG. 1) maintains the cavity 400 in an extended configuration to facilitate viewing, and helps to seal the incision through which the trocar or cannula and instrument 10 are inserted.

Once a vessel tributary branch 210 is observed or identified, the tip 100 is extended and manipulated manually or by actuating the actuator 30a (or 30b) to expose a cradle section 114 which traps, partially engulfs, grasps, positions, orients and secures the vessel tributary 210 as best seen in FIGS. 6 and 7. Preferably, the cradle section 114 includes a cradle arm or extension 121 which is disposed in a recess within the outer periphery of the shaft 12 (See FIG. 2B). As can be appreciated, the activation of the actuator 30a or 30b remotely (outside the incision) extends or retracts the cradle arm 121 which, in turn, deploys or retracts the cradle section 114.

In a preferred embodiment according to the present disclosure, an open slot or recess 122 is disposed about the outer periphery of the shaft 12. An outer tube 47 (see FIG. 2C) acts to slidingly, sealingly maintain the cradle arm 121 in position with the slot 122 during extension and retraction of the cradle section 114. Alternatively, the outer tube 47 and the cradle section 114 may be integrally associated with one another such that selective movement of the tube 47 relative to the shaft 12 deploys and selectively moves the cradle section 114. As can be appreciated, no recess is needed within the outer periphery of the shaft 12 in this latter embodiment since the tube 47 and the cradle section 114 move with one another.

Again, a gasket or lubricant may be employed between the shaft 12 and the tube 47 to provide a tight gaseous seal. Other seals (or the like) may also be used between additional instruments or components depending upon the particular embodiment, e.g., the shaft 12 and tube 47, or the shaft 12 and tube 47 and cannula 51.

In the embodiment shown in FIG. 2B, the cradle arm 121 is disposed within a self-enclosed slot 122 disposed near the outer periphery of shaft 12. Slot 122 may include a v-shaped cross section, u-shaped cross section, dove tail cross section or any other configuration to provide a controlled location and facilitate relative movement of the cradle arm within the slot 122. Moreover, the mechanical engagement of the cradle arm 121 within the slot 122 is preferably a tight, slip-friction fit to provide a gaseous seal. Additional components may also be included to enhance the gaseous seal, e.g., gasket(s), o-ring(s) and/or grease-like sealing lubricants. Moreover, the distal end 16b of the shaft 12 may include one or more of the above-identified sealing components to further promote a gaseous seal. For example, an o-ring type seal 57 may be attached to the proximal end of the cradle arm 121 to provide gaseous sealing between the cradle arm 121 and the outer periphery of the shaft 12.

The extension of the cradle section 114 exposes a gap or cutting cavity 125 between the cradle section 114 and the distal end 16b of the shaft 12. The cutting cavity 125 extends from a concave area or hollow 137 inside the blunt tip 100 to but preferably not through the distal end 16 of the shaft 12. This enables the ligating and/or cutting instrument (or other one of the plurality of instruments) to extend beyond the vessel tributary for positioning, manipulating and ligating/transecting or otherwise treating a vessel. In addition, the concave area 137 inside the blunt tip 100 may also be dimensioned to house the or a distal end or end portion of the additional instrument when the tip 100 is unexposed or fully retracted.

It is envisioned that the cradle section 114 may be operatively associated with a remote actuator, e.g., 31b, to allow selective movement along, and if desired, rotation of the cradle section 114 about a longitudinal axis of the instrument 10. In this embodiment, the tip 100, cradle section 114 and shaft 12 would rotate independently of and about the endoscope 162 (i.e., the endoscope 162 remains fixed) which allows the user to maintain a clear view of the working area and cutting cavity 125 throughout 360° of rotation of the cradle section 114 and shaft 12. Alternatively but less desirably, the cradle arm 121 may be fixed against rotation to prevent rotation of the cradle section 114 relative to the viewing lens 164 of the endoscope 162.

Figure 8:
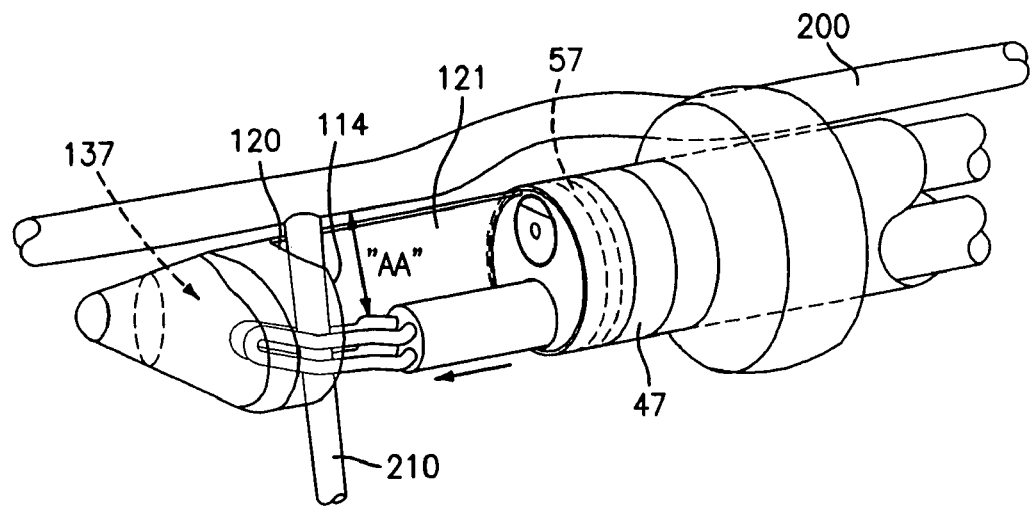
FIG. 8 is a perspective view of the harvesting instrument showing the ligation instrument ligating and cutting the vessel tributary from the main vessel.

The user then employs the trigger 130a (or 130b) to extend and/or rotate the ligating instrument 132 into the cutting cavity 125 and manipulates trigger handles 136 and 138 to grasp and secure the vessel branch 210 between the jaw members 134a and 134b (FIG. 8). Preferably, the ligating instrument 132 is selectively rotatable within its respective lumen 150b to facilitate use of the instrument relative to the vessels or branches.

As can be appreciated, the endoscope 162 provides a clear view of the cutting cavity 125 and vessel tributaries 210 to assure consistent and accurate manipulation of the jaw members 134a and 134b about a particular tributary branch 210. A light may also be employed with the endoscopic lens to illuminate the operating cavity and cutting cavity to facilitate dissection and harvesting. Preferably, the endoscope is oriented or adapted to view the working area and in some circumstances it may be desirable to orient the endoscope at an angle relative to the working area to enhance viewing. Electrosurgical energy is then applied to cut the vessel branch 210 from the vessel 200.

In a preferred embodiment, for viewing the arms of the ligating instrument, the endoscope 162 is directed or focused downward at an angle of about 30°. Alternatively, the endoscope may also be provided at a flat angle, i.e., 0° degrees, to enable a wider view of the operating area. It is envisioned that the instrument 10 may include a focusing lens which enables the surgeon to selectively orient or focus the endoscope 162 depending upon a particular purpose.

Figure 9:
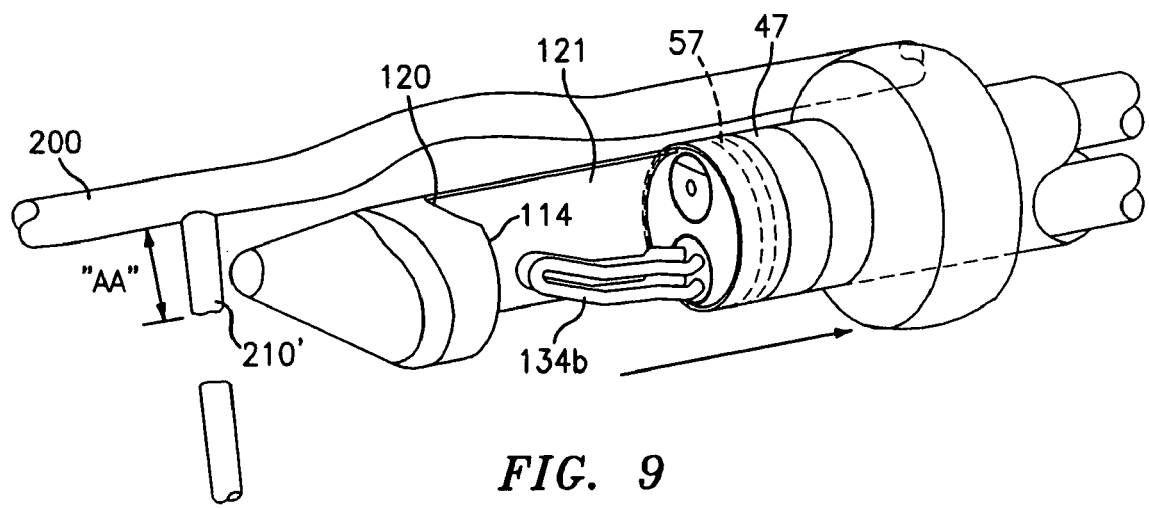
FIG. 9 is a perspective view of the harvesting instrument showing the separated vessel tributary outside of the cradle section.

Since jaw members 134a and 134b of the ligating instrument 132 are positioned a predetermined distance "AA" from the outer periphery of shaft 12 and, hence, from vessel 200, controlled, consistent and accurate ligations, transections and lengths and separations of the tributary 210 from the remaining branch vessel 210' are obtained without compromising the integrity or strength of vessel 200. This minimizes contact between instrument 10 and vessel 200 and controls and minimizes the amount of energy absorbed by vessel 200. Also, each remaining tributary branch 210 360° about the vessel 200 will be the same distance "AA" from main vessel 200. Once the tributary branch 210 is separated, the ligating instrument 132 and/or blunt tip 100 may, but need not be, be retracted (or retracted and extended as needed) to permit subsequent dissection of the remaining vessel 200 from the surrounding tissue 300 (FIG. 9).

Figure 10:
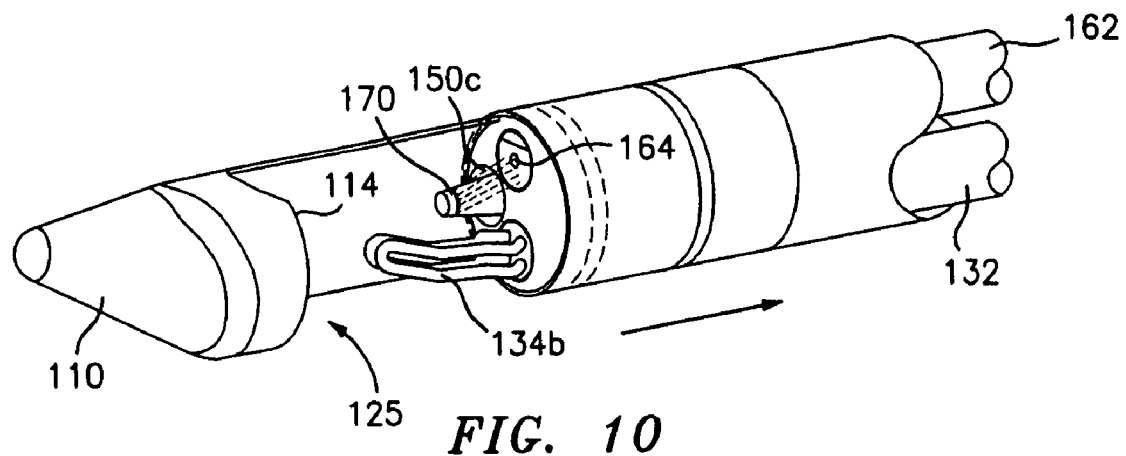
FIG. 10 is a perspective view of another embodiment of the present disclosure wherein the shaft includes an additional lumen for housing an additional instrument, e.g., an irrigation instrument for cleaning the lens of the endoscope.

As mentioned above, the shaft may include additional lumens 150c and 150d which can house additional surgical instruments, for example, for dissection of the surrounding tissue 300 and for removal of the branch tributaries 210. For example, FIG. 10 shows an irrigation nozzle 170 disposed in lumen 150c which may be selectively deployed to eject fluid therefrom to clean/clear operating fluids or debris from the endoscopic lens 164. This assures clear continual visualization of the operating cavity 400 and cutting cavity 125 without removal of the endoscope 162 for cleaning purposes. Other instruments may also be selectively utilized to facilitate dissection of the vessel 200 and/or separation of the vessel branches 210, e.g., suction instruments, clip appliers, scissors (mechanical, bipolar, ultrasonic, etc.) shears, insufflators, bipolar or ultrasonic vessel sealing instruments, etc. One lumen can be used as a channel member for passage of a fluid (gas or liquid) to inflate and/or deflate one or more balloons which may be employed to facilitate dissection and harvesting of the vessel 200.

Figure 12A:
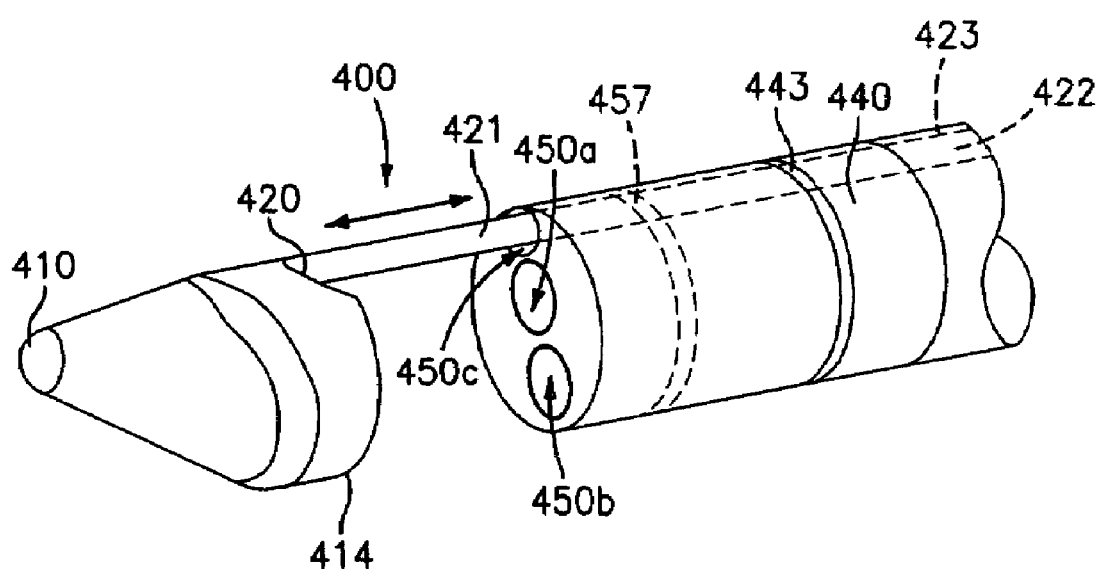
FIG. 12A shows an alternate embodiment of the movable tip and cradle section according to the present disclosure.

FIG. 12A shows another embodiment of a cradle arm, here designated 421, which is operatively associated with actuator 30a (or 30b) for example by utilizing rod member 422 which is recessed within an elongated slot-like depression 423 disposed about the outer periphery of the shaft. By actuating the actuator 30a (or 30b), the user can selectively expose and retract the cradle section 414 and tip 410 as needed during dissection and harvesting. This embodiment may also provide the user with the additional option of off-set rotation of the cradle section 414 relative to the shaft 12 which may prove useful for dissection purposes.

Figure 12B:
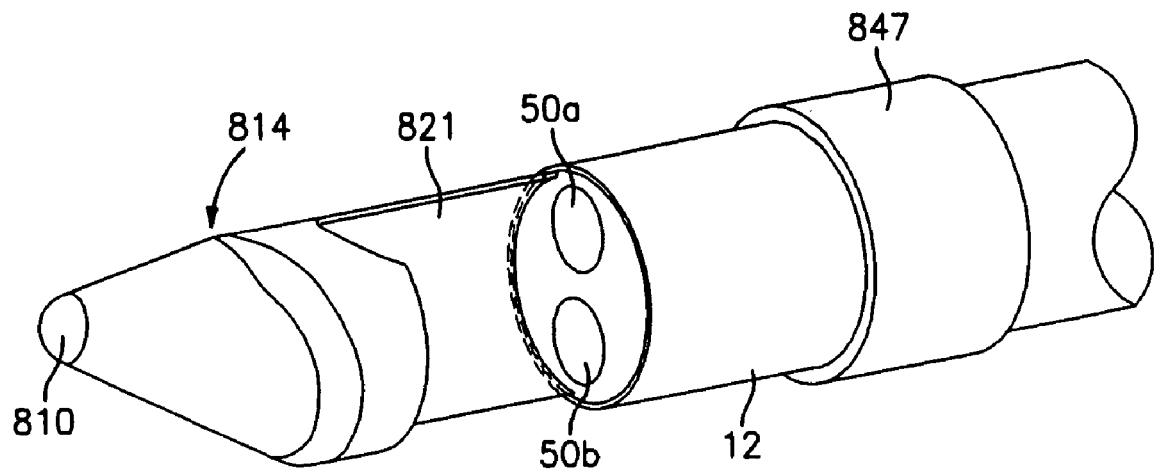
FIG. 12B shows an alternate embodiment of the movable tip and cradle section according to the present disclosure

As best shown in FIG. 12B, the tip 810 and/or cradle section 814 may include an arm or extension 821 coupled to a tube-like proximal portion or arm 847 which partly surrounds shaft 12. The tube-like proximal portion mechanically couples to the actuator 30a to enable selective extension, retraction and/or rotation of the cradle section 814 and tip 810.

Figure 13:
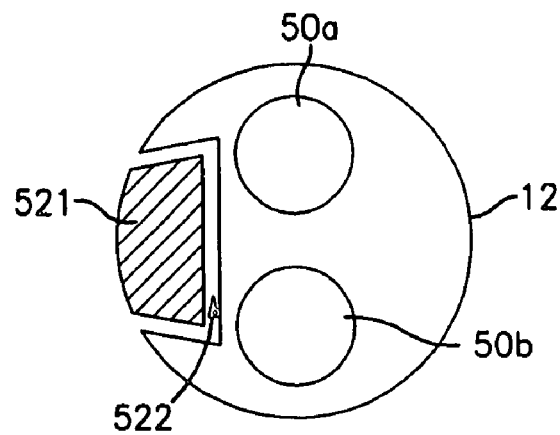
FIGS. 13-14 show alternate methods for slidingly engaging the cradle arm to the outer periphery of the shaft.
Figure 14:
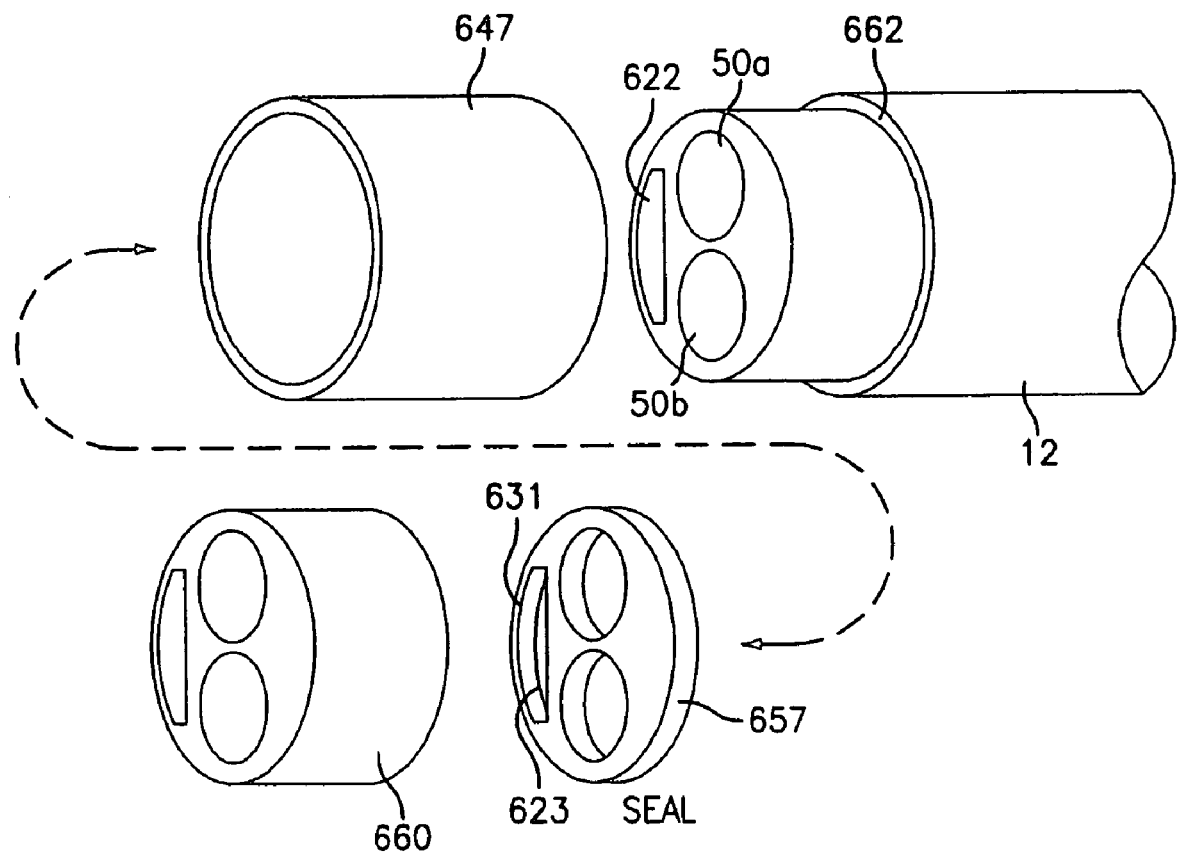
Figure 15:
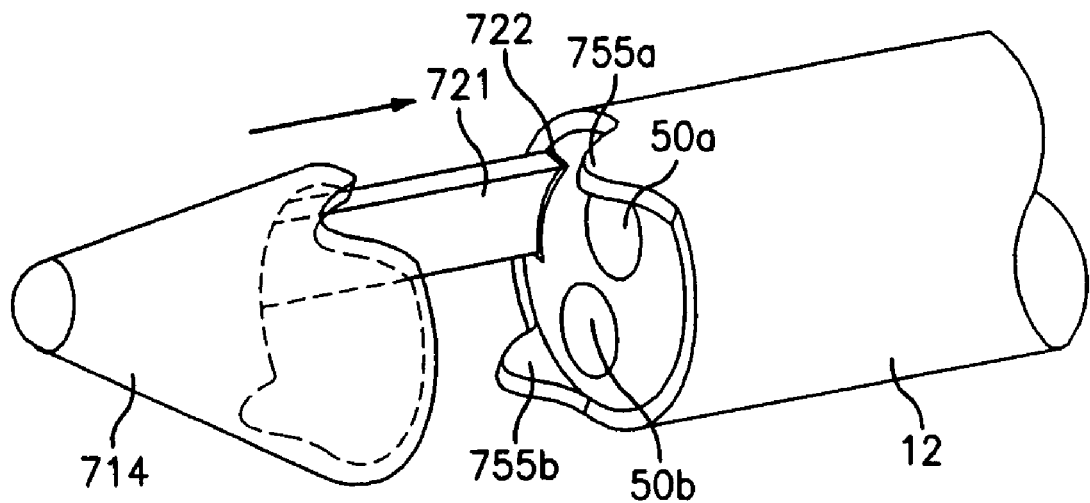
FIG. 15 shows an alternate embodiment of an instrument of the present invention, with parts broken away.

FIGS. 13-15 show alternate embodiments of the cradle arm 521 slidingly engaged within a recess or slot in shaft 12. FIG. 13 shows one embodiment wherein the cradle arm 521 includes a dove-tail cross section which mates with a corresponding recess 522 disposed within the outer periphery of shaft 12. As can be appreciated, the dove-tail cross section by design constrains the cradle arm 521 within the recess 522 without requiring an outer tube or sleeve to keep the arm seated therewithin. Suitable sealing means are employed to provide a gaseous seal between cradle arm 521 and recess 522.

FIG. 14 shows yet another embodiment for seating the cradle arm within the outer periphery of the shaft 12. A seal, here a gasket 657 is included to provide a gaseous seal between the shaft 12 and the tube 647. A rubber flange 631 may also be included about the inner periphery of the corresponding seal recess 623 to maintain the cradle arm in tight, slip-friction engagement during extension and retracting of the cradle arm. Further, a plug 660 may also be included to compress the seal 657 against the distal end of the shaft 12 to maintain gaseous integrity. In this and other embodiments, when a short tube 47 or 647 is employed, the tube may be seated and held or affixed if desired, within the reduced diameter distal end portion of shaft 12 against step 662 to provide a uniform diameter with the larger diameter of shaft 12.

FIG. 15 shows still another embodiment wherein the cradle arm 721 is generally rectilinear and slideably engages a corresponding recess disposed in the distal end of the shaft 12. As can be appreciated, the rectilinear design of the cradle arm 721 prevents rotation of the cradle arm 721 relative to the distal end of the shaft 12 and the endoscope (not shown) to avoid possibly obstructing the cutting cavity 725. A pair of alignment tabs 755a, 755b may also be included to facilitate alignment of the cradle section 714 when fully retracted against the distal end of the shaft 12. Tabs 755a, 755b when seated in the cut out portions of the cradle help to keep tissue and debris from falling into the working cavity between the distal face of shaft 12 and cradle section 714.

The present disclosure also relates to a method for harvesting a vessel 200 from surrounding tissue 300. The method includes the steps of: providing a surgical instrument 10 having a shaft housing 18' including distal and proximal ends 14 and 13, respectively. The housing 18' also includes an elongated shaft 12 attached at or extending from the distal end 14 which includes a blunt tip 100 and a plurality of lumens, e.g., 150a-150d disposed therethrough. Preferably, one of the lumens 150a is dimensioned to accommodate an endoscope 162 and one of the remaining plurality of lumens, e.g., 150b is dimensioned to accommodate one of a plurality of additional surgical instruments selected from the group consisting of: ligating instruments, bipolar instrument, ultrasonic instruments, clip appliers, coagulating instruments, cutting instruments, vessel sealing instruments, vessel graspers, insufflators, irrigation instruments and suction instruments. Blunt tip 100 is selectively movable to expose a cradle section 114 between the tip 100 and a distal end 16b of the shaft 12. Preferably, endoscope 162 and ligating/transecting instrument 132 are provided as part of instrument 10. The method can include providing a cannula or elongated sheath for housing therein the extendable and retractable shaft 12 or cradle arm 121 that includes blunt tip 100 and cradle 114. The endoscope and ligating instrument may be sold separately apart from the instrument 10.

The method of the present disclosure can comprise the steps of: inserting the instrument 10 into an incision in the body; advancing the instrument 10 through the incision and along the vessel 200; utilizing the endoscope 162 to view and blunt tip 100 to dissect surrounding tissue 300 from the vessel 200 and form an operating cavity; selectively extending the blunt tip 100 to dissect tissue and/or to expose the cradle section 114 to position, cradle or secure vessel tributaries 210 for treatment, e.g., ligation and transection by one or more of the additional surgical instruments; repeating the advancing and/or extending steps as needed to clear surrounding tissue 300 from the vessel 200 and treat vessel tributaries 210; and removing the vessel 200 from the operating cavity 400.

Dissection (preferably with the tip 100 retracted) can be performed while or in the process of moving the instrument 10 distally to effect and complete dissection in the distal direction, and vessel tributary treatment, e.g., ligation and transection, can be effected (preferably with the tip in the selectively extended position) while intermittently or otherwise moving or withdrawing the instrument and/or cradle 114 in the proximal direction.

Before or after the extending step, the method may include the step of: rotating the blunt tip 100 and cradle section 114 to position tributaries 210 for treatment. Preferably, the tip 100, the cradle section and the shaft including the ligating instrument are rotated about the endoscope 162. The shaft 12 of the providing step may include a balloon 40 attached to the outer periphery thereof, e.g., in a recess in the outer surface of shaft 12, or tube 47, and after the insertion step, the method may include the step of: selectively inflating the balloon 40 to further dissect surrounding tissue 300 from the vessel 200 to create a space 400 between the vessel 200 and surrounding tissue 300. Preferably, after the inflating step, the method includes the step of: insufflating the space 400 between the vessel 200 and surrounding tissue 300 with a fluid or gas.

The present disclosure also relates to a method for harvesting a vessel 200 from surrounding tissue 300 which includes the steps of: providing a surgical dissector 10 having a housing 18 or 18' in each case with distal and proximal ends (as mentioned above, housing 18 may be integral with shaft housing 18' or, alternatively, the shaft housing 18' may be the proximal end of instrument 10 and may be removably engaged with the housing 18). In such latter instance, the housing 18 would include an elongated shaft 12 supported by and attached at and/or extending distally from a distal end 14 of the overall housing 18 and 18' and which has a blunt tip 100 and at least one lumen 150a disposed therein for housing an endoscope 162. The tip 100 is selectively extendable from the shaft 12 to expose a cradle section 114 for positioning tributaries 210 of the vessel 200.

The method can include the steps of: inserting the instrument 10 into an incision in the body; advancing the instrument 10 through the incision and along the vessel 200 utilizing the endoscope 162 to view and the blunt tip 100 to dissect surrounding tissue 300 from the vessel 200; selectively extending the blunt tip 100 to expose the cradle section 114 and position a vessel tributary 210 thereon; and treating the vessel tributaries by utilizing one of the plurality of surgical instruments.

Additional steps of the method may include: repeating the advancing and extending steps as needed to clear surrounding tissue 300 from the vessel 200 and separate additional vessel tributaries 210; and removing the vessel 200 from the body.

Preferably, after the extending step, the method further includes the step of: rotating the blunt tip 100 and the cradle section 114 to position and orient vessel tributaries 210 for treatment.

From the foregoing and with reference to the various figure drawings, those skilled in the art will appreciate that certain modifications can also be made to the present disclosure without departing from the scope of the present disclosure. For example, it is contemplated that the presently disclosed instrument 10 may include a disposable shaft 12 which is selectively operatively engageable with the shaft housing 18'

(or base housing 18 if integral with shaft housing 18') and/or a disposable tip 100 (with or without a cradle) which is selectively operatively engageable with the distal end 16b of the shaft 12. Moreover, the instrument 10 may utilize either electrosurgical cutting instruments or non-electrical cutting instruments to separate the vessel branches 210 from the vessel 200 depending upon a particular purpose or to achieve a particular result, e.g., scissors.

Figure 16:
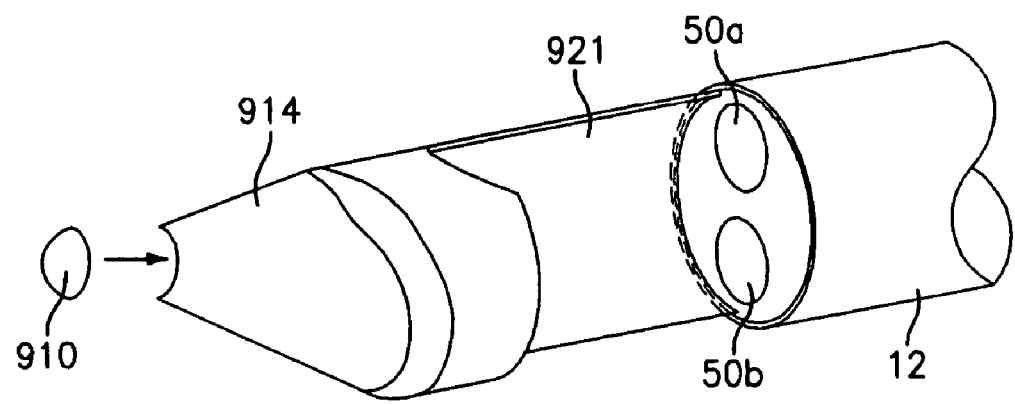
FIG. 16 shows an alternate embodiment of a cradle section with a selectively removable tip according to the present disclosure.
Figure 17:
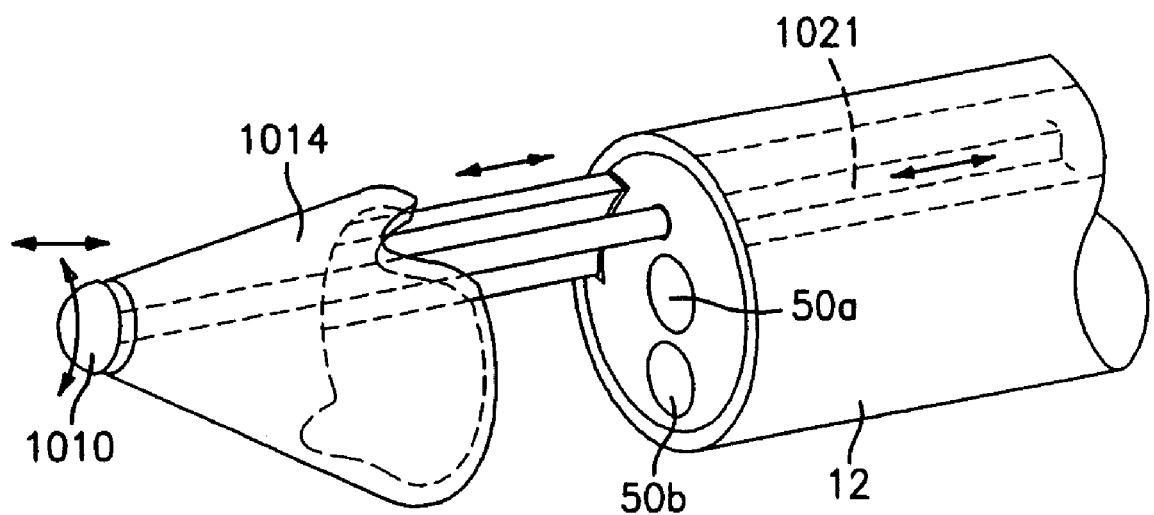
FIG. 17 shows an alternate embodiment of the cradle section with an independently movable tip according to the present disclosure.

It is envisioned that the instrument may be designed such that the blunt tip 910 is removably engageable with the cradle section 914 thus allowing a surgeon to selectively engage variously-sized and variously-shaped tips for dissection purposes (See FIG. 16). Moreover, the instrument may be designed such that the blunt tip 1010 is independently operable, i.e., extendible, retractable and/or rotatable via arm 1021, relative to the cradle section 1014 (See FIG. 17).

Whether instrument 10 comprises its components extending distally from the proximal end of shaft housing 18' apart from or connected to or as part of the structure located proximally of the proximal end of shaft housing 18', preferably the aforementioned components excluding endoscope 162 are rotatable about the endoscope, and the endoscope and aforementioned structure is not rotatable.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A method for harvesting a vessel from surrounding tissue, comprising the steps of:
    providing a surgical instrument having:
        a housing including distal and proximal ends, said housing having an elongated shaft attached thereto and extending from a distal end thereof, said shaft including a tip and a plurality of lumens disposed through portions thereof, one of said lumens being dimensioned to accommodate an endoscope, and at least one of said remaining plurality of lumens being dimensioned to accommodate one of a plurality of additional surgical instruments selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same;
        said tip having a distal blunt section and a proximal notched portion, the tip being selectively movable to expose a cradle section, said cradle section being located between the proximal notched portion of said tip and a distal end of said shaft, said proximal notched portion oriented transversely to the longitudinal axis of the shaft and dimensioned to facilitate grasping of a vessel tributary;
    inserting said instrument into an incision in the body;
    advancing said instrument through the incision and along the vessel;
    utilizing the endoscope to view and the blunt tip to dissect surrounding tissue from the vessel to form an operating cavity;
    extending said blunt tip to expose said cradle section;
    positioning vessel tributaries in said cradle section for treatment by one of the plurality of additional surgical instruments; and
    positioning said vessel tributaries in the notched portion for treatment by one of the plurality of additional surgical instruments; and
    treating said vessel tributaries by use of said one of said plurality of surgical instruments.

2. A method according to claim 1 wherein said additional instrument includes an electrosurgical ligation instrument.

3. A method according to claim 2 wherein said housing includes a trigger for selectively activating said electrosurgical ligation instrument.

4. A method according to claim 1 wherein one of the plurality of the lumens accommodates an irrigation and suction device.

5. A method according to claim 1 wherein said housing includes an actuator for selectively extending and retracting said blunt tip.

6. A method according to claim 5 wherein said elongated shaft of said providing step includes a longitudinal axis defined therethrough and said actuator extends and retracts said blunt tip along or parallel to said longitudinal axis and said actuator is for rotating said blunt tip and said cradle section relative to said endoscope.

7. A method according to claim 5 wherein said method further comprises the step of:
    rotating said blunt tip, cradle section and said shaft relative to and about said endoscope to position vessel tributaries in said cradle section for treatment.

8. A method according to claim 1 wherein said blunt tip of said providing step is conical.

9. A method according to claim 1 wherein said blunt tip of said providing step is transparent.

10. A method according to claim 1 wherein said endoscope of said providing step is integrally associated with said housing.

11. A method according to claim 1 wherein said endoscope of said providing step is engageable with said housing.

12. A method according to claim 1 wherein said elongated shaft of said providing step is selectively engageable with said shaft housing.

13. A method according to claim 1 wherein said one of said plurality of said additional instruments is a ligating instrument and said ligating instrument is provided as part of the instrument.

14. A method according to claim 1 wherein said shaft of said providing step includes a balloon disposed on an outer periphery thereof.

15. A method according to claim 14 wherein after said inserting step the method further comprises the step of:
    selectively inflating said balloon to further dissect surrounding tissue from the vessel to create a space between the vessel and surrounding tissue.

16. A method according to claim 15 wherein after said inflating step the method further comprises the step of:
    insufflating the space between the vessel and surrounding tissue with a fluid.

17. A method according to claim 1 wherein said cradle section and said blunt tip of said providing step are rotatable about said endoscope.

18. A method according to claim 1 wherein said shaft of said providing step is rotatable about said endoscope.

19. A method according to claim 1 wherein said provided housing is a shaft housing, said instrument is also provided with a base housing located proximally relative to said shaft housing, said endoscope of said providing step is engageable with said base housing, and said shaft housing and said base housing are selectively engageable with one another.

20. A method for harvesting a vessel from surrounding tissue, comprising the steps of:
providing a surgical instrument having:
a housing including distal and proximal ends, said housing having an elongated shaft attached thereto and extending from a distal end thereof, said shaft including a tip and a plurality of lumens disposed through at least portions of said shaft, one of said lumens being dimensioned to accommodate an endoscope, and at least one of said remaining plurality of lumens being dimensioned to accommodate one of a plurality of additional surgical instruments selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same;
said tip having a distal blunt section and a proximal notched portion, the tip being selectively distally extendible from a retracted position to expose a cradle section, said cradle section being located between the proximal notched portion of said tip and a distal end of said shaft, said proximal notched portion oriented transversely to the longitudinal axis of the shaft and dimensioned to facilitate grasping of a vessel tributary;
inserting said instrument into an incision in the body;
advancing said instrument distally through the incision and along the vessel with said tip in a retracted position with the cradle section substantially unexposed;
utilizing the endoscope to view and the blunt tip to dissect surrounding tissue from the vessel to form an operating cavity;
selectively extending said blunt tip to expose said cradle section;
retracting said instrument in a proximal direction toward said incision and utilizing said exposed cradle section to position vessel tributaries in the notched portion for treatment by one of the plurality of additional surgical instruments; and
treating said vessel tributaries by use of said one of said plurality of surgical instruments.

21. A method for harvesting a vessel from surrounding tissue, comprising the steps of:
providing a surgical dissector having:
a housing including distal and proximal ends, said housing having an elongated shaft attached thereto and extending from a distal end thereof, said shaft including a tip and at least one lumen disposed through at least a portion of said shaft for housing an endoscope, said tip having a distal blunt section and a proximal notched portion, the tip being selectively distally extendable from said shaft to expose a cradle section for positioning vessel tributaries, said proximal notched portion oriented transversely to the longitudinal axis of the shaft and dimensioned to facilitate grasping of a vessel tributary;
inserting said dissector into an incision in the body;
advancing said dissector through the incision and along the vessel utilizing the endoscope to view and said tip to dissect surrounding tissue from the vessel;
selectively extending said tip to expose said cradle section and position a vessel tributary in said notched portion; and
ligating and separating the tributary from the vessel.

22. A method according to claim 21 wherein after said ligating and separating step, the method further comprises the step of:
repeating said advancing and extending steps as needed to clear surrounding tissue from the vessel and ligate and separate additional tributaries from the vessel.

23. A method according to claim 21 wherein said shaft of said providing step further includes providing said shaft with at least one additional lumen disposed therethrough for housing at least one additional instrument selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same.

24. A method according to claim 23 wherein said providing step includes providing an electrosurgical ligation instrument for ligating and separating tributaries from the vessel.

25. A method according to claim 23 wherein said providing step includes providing an irrigation and suction device.

26. A method according to claim 21 wherein said method further comprises the step of:
rotating said blunt tip and said cradle section to position tributaries for treatment.

27. A method according to claim 21 wherein said providing step includes providing a balloon attached to an outer periphery of said shaft.

28. A method according to claim 27 wherein after said advancing step the method further comprises the step of:
selectively inflating said balloon to further dissect surrounding tissue from the vessel to create a space between the vessel and surrounding tissue.

29. A method according to claim 28 wherein after said inflating step the method further comprises the step of:
insufflating the space between the vessel and surrounding tissue with a fluid.

30. A method for harvesting a vessel from surrounding tissue, comprising the steps of:
providing a surgical instrument having:
a housing including distal and proximal ends, said housing having an elongated shaft attached thereto and extending from a distal end thereof, said shaft including a tip and a plurality of lumens disposed through at least portions of said shaft, one of said lumens being dimensioned to accommodate an endoscope, and at least one of said remaining plurality of lumens being dimensioned to accommodate one of a plurality of additional surgical instruments selected from the group consisting of: ligating instruments, bipolar shears, ultrasonic shears, clip appliers, coagulating instruments, cutting instruments, vessel sealing instruments, vessel graspers, insufflators, irrigation instruments, suction instruments and combinations of the same;
said tip having a distal blunt section and a proximal notched portion, the tip being selectively distally extendible from a retracted position to expose a cradle section, said cradle section being located between the proximal notched portion of said tip and a distal end of said shaft, said proximal notched portion oriented transversely to the longitudinal axis of the shaft and dimensioned to facilitate grasping of a vessel tributary;
inserting said instrument into an incision in the body;
advancing said instrument distally through the incision and along the vessel with said tip in a retracted position with the cradle section substantially unexposed;

utilizing the endoscope to view and the tip to dissect surrounding tissue from the vessel to form an operating cavity;

retracting said instrument in a proximal direction toward said incision;

extending said tip to expose said cradle section;

re-advancing said instrument distally through said incision and along the vessel with the cradle section exposed;

utilizing said exposed cradle section to successively position respective vessel tributaries in said notched portion; and treating said successive cradled vessel tributaries by use of said one of said plurality of additional surgical instruments.

31. The method according to claim 30, wherein there is included the additional steps of:

incising a length of the vessel; and removing the vessel length.

* * * * *